(12) United States Patent
Naidu et al.

(10) Patent No.: US 7,115,601 B2
(45) Date of Patent: Oct. 3, 2006

(54) HIV INTEGRASE INHIBITORS

(75) Inventors: B. Narasimhulu Naidu, Durham, CT (US); Margaret E. Sorenson, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/127,878

(22) Filed: May 12, 2005

(65) Prior Publication Data

US 2005/0261322 A1    Nov. 24, 2005

Related U.S. Application Data

(60) Provisional application No. 60/572,048, filed on May 18, 2004.

(51) Int. Cl.
*C07D 221/20* (2006.01)
*A61K 31/506* (2006.01)
*C07D 239/60* (2006.01)

(52) U.S. Cl. .................. 514/228.8; 514/249; 514/273; 544/71; 544/320; 544/321

(58) Field of Classification Search .................. 544/71, 544/320, 321; 514/228.8, 249, 273
See application file for complete search history.

(56) References Cited

U.S. PATENT DOCUMENTS

| 2004/0229909 | A1 | 11/2004 | Kiyama et al. |
| 2005/0054645 | A1 | 3/2005 | Miyzaki et al. |
| 2005/0204498 | A1* | 9/2005 | Saunders et al. .............. 15/172 |

FOREIGN PATENT DOCUMENTS

| JP | 2004/244320 | 9/2004 |
| WO | WO2001/70829 | 9/2001 |
| WO | WO2002/070491 | 12/2002 |
| WO | WO2003/35076 | 5/2003 |
| WO | WO2003/35077 | 5/2003 |
| WO | WO2004/058756 | 7/2004 |
| WO | WO2004/058757 | 7/2004 |
| WO | WO2004/062613 | 7/2004 |
| WO | WO2004/096128 | 11/2004 |
| WO | WO2005/061490 | 7/2005 |
| WO | WO2005/061501 | 7/2005 |
| WO | WO2005/070901 | 8/2005 |
| WO | WO2005/113562 | 12/2005 |
| WO | WO2005/118589 | 12/2005 |
| WO | WO2005/118590 | 12/2005 |
| WO | WO2005/118593 | 12/2005 |

OTHER PUBLICATIONS

Miles et al., Medline Abstract (The growing of HIV pandemic, Community Pract vol. 78, Issue 8, pp. 292-294) Aug. 2005.*
Ulrich, Chapter 4: Crystallization, Kirk-Othmer Encyclopedia of Chemical Technology, Aug. 2002.*
Marcus et al., PubMed Abstract (Intervirology, 45(4-6):260-6), 2002.*
Van Heeswijk et al., PubMed Abstract (Antivir Ther 6(4):201-29) Dec. 2001.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
U.S. Appl. No. 11/227,526, filed Sep. 16, 2004, Krystal et al.
Neamati, N., "Patented small molecule inhibitors of HIV-1 integrase: a 10-year saga," Expert Opinion, vol. 12, No. 5, pp. 709-724 (2002).
Godwin, C.G.P. et al, "Novel aryl diketo-containing inhibitors of HIV-1 integrase," Drugs of the Future, vol. 27, No. 11, pp. 1101-1111 (2002).
Sunderland, C.J. et al, "6-Carboxamido-5,4-Hydroxyprimidinones: A New Class of Heterocyclic Ligands and Their Evaluation as Gadolinium Chelating Agents," Inorg. Chemistry, vol. 40, pp. 6746-6756 (2001).

* cited by examiner

*Primary Examiner*—Deepak Rao
(74) *Attorney, Agent, or Firm*—Pamela A. Mingo; James Epperson

(57) ABSTRACT

Compounds of the present disclosure are spirocycle-substituted pyrimidinecarboxamides. Also disclosed are pharmaceutical compositions comprising the compounds, and methods of using the compounds. The compounds are useful for treating HIV infection and AIDS.

11 Claims, No Drawings

HIV INTEGRASE INHIBITORS

CROSS REFERENCE TO RELATED APPLICATION

The present application claims the benefit of priority under 35 U.S.C. § 119(e) from U.S. provisional application 60/572,048, filed May 18, 2004.

The present disclosure describes novel spirocycle-substituted pyrimidinecarboxamides, their pharmaceutical compositions, and methods of use. The compounds are useful for treating HIV infection and AIDS.

Human immunodeficiency virus (HIV) has been identified as the etiological agent responsible for acquired immune deficiency syndrome (AIDS), a fatal disease characterized by destruction of the immune system and the inability to fight life-threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the U.S., where combination therapy is widely available, the number of HIV-related deaths has declined (N. Engl. J. Med. 1998, 338, 853–860).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regimen as well as intrinsic pharmacological barriers to exposure provides fertile ground for resistance to emerge. More disturbing are recent findings which suggest that low-level replication continues even when viral plasma levels have dropped below detectable levels (<50 copies/mL) (JAMA 2000, 283, 381–390). Clearly there is a need for new antiviral agents, such as those targeting other viral enzymes to reduce the rate of resistance and suppress viral replication even further.

HIV expresses three enzymes: reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Science 2000, 284, 646). Recently, HIV integrase inhibitors have been accepted into clinical trials for treating AIDS and HIV infections (Expert. Opin. Ther. Patents 2002, 12, 709; Drugs Fut. 2002, 27, 1101).

In one embodiment the present disclosure provides a compound of formula (I)

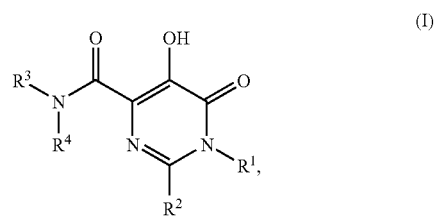

and/or a pharmaceutically acceptable salt and/or solvate thereof, wherein $R^1$ is selected from hydrogen, alkenyl, alkoxyalkyl, alkyl, and arylalkyl;

$R^2$ is a 3- to 8-membered saturated or partially unsaturated ring containing one to three heteroatoms selected from N, O, and $S(O)_n$, wherein n is 0, 1, or 2; wherein said ring is attached to the parent compound through one of its heteroatoms, and wherein said ring is substituted by a 3- to 10-membered monocyclic or bicyclic spirocycle containing from zero to three heteroatoms selected from N, O, and $S(O)_n$, wherein n is 0, 1, or 2; and wherein said ring and said spirocycle are each optionally substituted with one to three substituents independently selected from alkoxy, alkyl, alkylcarbonyl, aryl, halo, heteroaryl, heterocyclyl, —$NR^aR^b$, oxo, thiooxo, and trialkylsilyl;

$R^3$ and $R^4$ are independently selected from hydrogen, aryl, arylalkyl, heteroaryl, heteroarylalkyl, heterocyclyl, and heterocyclylalkyl; and $R^a$ and $R^b$ are independently selected from hydrogen, alkyl, aryl, and arylalkyl.

In another embodiment the present disclosure provides a compound of formula (I) wherein $R^1$ is alkyl and $R^2$, $R^3$, $R^4$, $R^a$, and $R^b$ are as described for formula (I).

In another embodiment the present disclosure provides a compound of formula (I) wherein $R^3$ and $R^4$ are independently selected from hydrogen and arylalkyl and $R^1$, $R^2$, $R^a$, and $R^b$ are as described for formula (I).

In another embodiment the present disclosure provides a compound of formula (II),

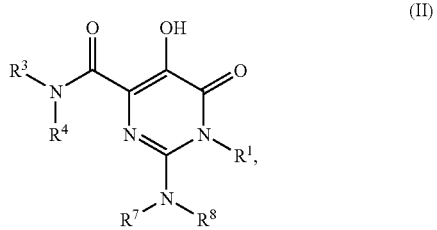

and/or a pharmaceutically acceptable salt and/or solvate thereof, wherein $R^1$ is selected from hydrogen, alkenyl, alkoxyalkyl, alkyl, and arylalkyl;

$R^3$ and $R^4$ are independently selected from hydrogen, aryl, arylalkyl, heteroaryl, heteroarylalkyl, heterocyclyl, and heterocyclylalkyl;

$R^7$ and $R^8$, together with the nitrogen atom to which they are attached, form a 3- to 8-membered saturated or partially unsaturated ring containing zero to two additional heteroatoms selected from N, O, and $S(O)_n$, wherein n is 0, 1, or 2; wherein said ring is substituted by a 3- to 10-membered monocyclic or bicyclic spirocycle containing from zero to three heteroatoms selected from N, O, and $S(O)_n$, wherein n is 0, 1, or 2; and wherein said ring and said spirocycle are each optionally substituted with one to three substituents independently selected from alkoxy, alkyl, alkylcarbonyl, aryl, halo, heteroaryl, heterocyclyl, —$NR^aR^b$, oxo, thiooxo, and trialkylsilyl; and $R^a$ and $R^b$ are independently selected from hydrogen, alkyl, aryl, and arylalkyl.

In another embodiment the present disclosure provides a compound of claim formula (II) wherein $R^1$ is alkyl and $R^2$, $R^3$, $R^4$, $R^a$, and $R^b$ are as described for formula (II).

In another embodiment the present disclosure provides a compound of formula (II) wherein $R^3$ and $R^4$ are independently selected from hydrogen and arylalkyl and $R^1$, $R^2$, $R^a$, and $R^b$ are as described in formula (II).

In another embodiment the present disclosure provides a compound of formula (II) wherein $R^1$ is alkyl;

$R^3$ and $R^4$ are independently selected from hydrogen, and arylalkyl; and $R^7$ and $R^8$, together with the nitrogen atom to which they are attached, form piperidinyl ring substituted by a 5- to 9-membered monocyclic or bicyclic spirocycle containing from zero to three heteroatoms selected from N, O, and $S(O)_n$, wherein n is 0, 1, or 2; and wherein said piperidinyl and said spirocycle are each optionally substituted with one to three substituents independently selected from alkoxy, alkyl, alkylcarbonyl, aryl, halo, heteroaryl, heterocyclyl, —$NR^aR^b$, oxo, thiooxo, and trialkylsilyl.

In another embodiment the present disclosure provides a compound selected from 2-(1,4-dioxa-8-azaspiro[4.5]dec-8-yl)-N-[(4-fluorophenyl)methyl]-1,6-dihydro-5-hydroxy-1-methyl-6-oxo-4-pyrimidinecarboxamide;

2-(1,4-dioxa-8-azaspiro[4.5]dec-8-yl)-N-[(4-fluoro-3-methylphenyl)methyl]-1,6-dihydro-5-hydroxy-1-methyl-6-oxo-4-pyrimidinecarboxamide;

N-[(4-fluorophenyl)methyl]-1,6-dihydro-5-hydroxy-1-methyl-6-oxo-2-(4-oxo-1-phenyl-1,3,8-triazaspiro[4.5]dec-8-yl)-4-pyrimidinecarboxamide;

N-[(4-fluoro-3-methylphenyl)methyl]-1,6-dihydro-5-hydroxy-1-methyl-6-oxo-2-(4-oxo-1-phenyl-1,3,8-triazaspiro[4.5]dec-8-yl)-4-pyrimidinecarboxamide;

N-[(4-fluoro-3-methylphenyl)methyl]-1,6-dihydro-5-hydroxy-1-methyl-2-(2-methyl-1-oxo-2,8-diazaspiro[4.5]dec-8-yl)-6-oxo-4-pyrimidinecarboxamide;

N-[(4-fluoro-3-methylphenyl)methyl]-1,6-dihydro-5-hydroxy-1-methyl-2-(3-oxa-8-azaspiro[5.5]undec-8-yl)-6-oxo-4-pyrimidinecarboxamide;

N-[4-fluoro-3-methylphenyl)methyl]-2-(1,3-diethyl-2,4-dioxo-1,3,8-triazaspiro[4.5]dec-8-yl)-1,6-dihydro-5-hydroxy-1-methyl-6-oxo-4-pyrimidinecarboxamide;

N-[4-fluoro-3-methylphenyl)methyl]-1,6-dihydro-2-(2,4-dioxo-1,3,8-triazaspiro[4.5]dec-8-yl)-5-hydroxy-1-methyl-6-oxo-4-pyrimidinecarboxamide;

N-[(4-fluoro-3-methylphenyl)methyl]-2-(3,4-benzo-2-oxo-8-azaspiro[4.5]decan-2-yl)-1,6-dihydro-5-hydroxy-1-methyl-6-oxo-4-pyrimidinecarboxamide;

N-[(4-fluoro-3-methylphenyl)methyl]-2-(8-azaspiro[4.5]dec-8-yl)-1,6-dihydro-5-hydroxy-1-methyl-6-oxo-4-pyrimidinecarboxamide;

N-[(4-fluoro-3-methylphenyl)methyl]-2-[3-[[(4-fluoro-3-methylphenyl)methyl]amino]spiro[1H-indene-1,4'-piperidin]-1'-yl]-1,6-dihydro-5-hydroxy-1-methyl-6-oxo-4-pyrimidinecarboxamide;

N-[(4-fluoro-3-methylphenyl)methyl]-2-(8-azaspiro[4.5]dec-8-yl)-1,6-dihydro-5-hydroxy-1-methyl-6-oxo-4-pyrimidinecarboxamide;

N-(4-fluoro-3-methylbenzyl)-5-hydroxy-1-methyl-6-oxo-2-(1-ethanone)-2,8-diazaspiro[4.5]dec-8-yl)-1,6-dihydropyrimidine-4-carboxamide;

N-(4-fluoro-3-methylbenzyl)-5-hydroxy 1-methyl-6-oxo-2-(1-trimethylsilane-6-azaspiro[4.3]oct-6-yl)-1,6-dihydropyrimidine-4-carboxamide;

N-(4-fluoro-3-methylbenzyl)-5-hydroxy-1-methyl-6-oxo-2-(6-azaspiro[4.3]oct-6-yl)-1,6-dihydropyrimidine-4-carboxamide;

N-[(4-fluoro-3-methylphenyl)methyl]-1,6-dihydro-5-hydroxy-1-methyl-2-(1-oxa-8-azaspiro[4.5]dec-8-yl)-6-oxo-4-pyrimidinecarboxamide.

In another embodiment the present disclosure provides a compound selected from

N-[(4-fluorophenyl)methyl]-1,6-dihydro-5-hydroxy-1-methyl-6-oxo-2-(7-azaspiro[4.5]dec-7-yl)-4-pyrimidinecarboxamide;

N-[(4-fluorophenyl)methyl]-1,6-dihydro-5-hydroxy-1-methyl-6-oxo-2-(6-oxa-9-azaspiro[4.5]dec-9-yl)-4-pyrimidinecarboxamide;

N-[(4-fluorophenyl)methyl]-1,6-dihydro-5-hydroxy-1-methyl-6-oxo-2-(2-oxa-7-azaspiro[4.5]dec-7-yl)-4-pyrimidinecarboxamide;

N-[(4-fluorophenyl)methyl]-1,6-dihydro-5-hydroxy-1-methyl-6-oxo-2-(1,3-dioxo-2,7-diazaspiro[4.5]dec-7-yl)-4-pyrimidinecarboxamide;

N-[(4-fluorophenyl)methyl]-1,6-dihydro-5-hydroxy-1-methyl-6-oxo-2-(2-oxo-1,7-diazaspiro[4.5]dec-7-yl)-4-pyrimidinecarboxamide;

N-[(4-fluorophenyl)methyl]-1,6-dihydro-5-hydroxy-1-methyl-6-oxo-2-(2,4-dioxo-1,3,8-triazaspiro[4.5]dec-8-yl)-4-pyrimidinecarboxamide;

N-[(4-fluorophenyl)methyl]-1,6-dihydro-5-hydroxy-1-methyl-6-oxo-2-(8-azaspiro[4.5]dec-8-yl)-4-pyrimidinecarboxamide;

N-[(4-fluorophenyl)methyl]-1,6-dihydro-5-hydroxy-1-methyl-6-oxo-2-(1-oxa-8-azaspiro[4.5]dec-8-yl)-4-pyrimidinecarboxamide;

N-[(4-fluorophenyl)methyl]-1,6-dihydro-5-hydroxy-1-methyl-6-oxo-2-(1-oxo-2,8-diazaspiro[4.5]dec-8-yl)-4-pyrimidinecarboxamide;

N-[(4-fluorophenyl)methyl]-1,6-dihydro-5-hydroxy-1-methyl-6-oxo-2-(2-oxo-1,3,8-triazaspiro[4.5]dec-8-yl)-4-pyrimidinecarboxamide;

N-[(4-fluorophenyl)methyl]-1,6-dihydro-5-hydroxy-1-methyl-6-oxo-2-(1,3,8-triazaspiro[4.5]deca-1,3-dien-8-yl)-4-pyrimidinecarboxamide;

N-[(4-fluorophenyl)methyl]-1,6-dihydro-5-hydroxy-1-methyl-6-oxo-2-(3-oxa-9-azaspiro[5.5]undec-9-yl)-4-pyrimidinecarboxamide;

N-[(4-fluorophenyl)methyl]-1,6-dihydro-5-hydroxy-1-methyl-6-oxo-2-(1-oxa-9-azaspiro[5.5]undec-9-yl)-4-pyrimidinecarboxamide;

N-[(4-fluorophenyl)methyl]-1,6-dihydro-5-hydroxy-1-methyl-6-oxo-2-(1-oxa-3,8-diazaspiro[4.5]dec-2-en-8-yl)-4-pyrimidinecarboxamide;

N-[(4-fluorophenyl)methyl]-1,6-dihydro-5-hydroxy-1-methyl-6-oxo-2-(1-oxa-4,9-diazaspiro[5.5]undec-9-yl)-4-pyrimidinecarboxamide;

N-[(4-fluorophenyl)methyl]-1,6-dihydro-5-hydroxy-1-methyl-6-oxo-2-(5-oxo-1-oxa-4,9-diazaspiro[5.5]undec-9-yl)-4-pyrimidinecarboxamide;

N-[(4-fluorophenyl)methyl]-1,6-dihydro-5-hydroxy-1-methyl-6-oxo-2-(1,4,9-triazaspiro[5.5]undec-9-yl)-4-pyrimidinecarboxamide; and N-[(4-fluorophenyl)methyl]-1,6-dihydro-5-hydroxy-1-methyl-6-oxo-2-(5-oxo-1,4,9-triazaspiro[5.5]undec-9-yl)-4-pyrimidinecarboxamide.

In another embodiment the present disclosure provides a composition comprising a pharmaceutically acceptable amount of a compound of formula (I), and/or a pharmaceutically acceptable salt thereof, and a pharmaceutically acceptable carrier.

In another embodiment the present disclosure provides a method for inhibiting HIV integrase comprising contacting a compound of formula (I), and/or a pharmaceutically acceptable salt thereof, with HIV integrase.

In another embodiment the present disclosure provides a method of inhibiting HIV viral DNA integration into human DNA comprising administering an effective amount of a compound of formula (I) to a cell infected with HIV.

In another embodiment the present disclosure provides a method of treating HIV infection in a patient comprising administering a therapeutically effective amount of a compound of formula (I). In another embodiment the method further comprises administering a therapeutically effective amount of one or more other HIV treatment agents selected from HIV protease inhibitors, HIV nucleoside reverse transcriptase inhibitors, HIV non-nucleoside reverse transcriptase inhibitors, HIV-entry inhibitors, HIV integrase inhibitors immunomodulators, or a combination thereof.

As used in the present specification the following terms have the meanings indicated:

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond. Examples of alkenyl groups include, but are not limited to, ethenyl, 2-propenyl, and isobutenyl.

The term "alkenylene," as used herein, refers to a divalent group derived from a straight or branched chain hydrocarbon containing at least one double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkyl," as used herein, refers to a group derived from a straight or branched chain saturated hydrocarbon containing from one to six carbon atoms. Examples of alkyl groups include, but are not limited to, methyl, ethyl, isopropyl, and tert-butyl.

The term "alkylcarbonyl," as used herein, refers to an alkyl group attached to the parent molecular moiety through a carbonyl group.

The term "alkylene," as used herein, refers to a divalent group derived from a straight or branched chain saturated hydrocarbon.

The term "aryl," as used herein, refers to a phenyl group, or a bicyclic or tricyclic fused ring system wherein one or more of the rings is a phenyl group. Bicyclic fused ring systems consist of a phenyl group fused to a monocyclic cycloalkenyl group, a monocyclic cycloalkyl group, or another phenyl group. Tricyclic fused ring systems consist of a bicyclic fused ring system fused to a monocyclic cycloalkenyl group, a monocyclic cycloalkyl group, or another phenyl group. The aryl groups of the present disclosure can be attached to the parent molecular moiety through any substitutable carbon atom in the group. Representative examples of aryl groups include, but are not limited to, anthracenyl, azulenyl, bicyclooctatrienyl, fluorenyl, indanyl, indenyl, naphthyl, phenyl, and tetrahydronaphthyl. The aryl groups of the present disclosure can be optionally substituted with one, two, three, four, or five substituents independently selected from alkenyl, alkoxy, alkyl, halo, haloalkoxy, haloalkyl, hydroxy, and oxo.

The term "arylalkyl," as used herein, refers to an alkyl group substituted with one, two, or three aryl groups.

The term "carbonyl," as used herein, refers to —C(O)—.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, adamantyl, bicyclo[3.1.1] heptyl, cyclobutyl, cyclopentyl, and cyclopropyl.

The terms "halo," and "halogen," as used herein, refer to Br, Cl, F, or I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "heteroalkenylene," as used herein, refers to a divalent group of two to eight atoms derived from a straight or branched chain that has at least one double bond and contains one or two heteroatoms independently selected from nitrogen, oxygen, and sulfur, wherein the remaining atoms are carbon. The heteroalkylene groups of the present disclosure can be attached through the carbon atoms or the heteroatoms in the chain.

The term "heteroalkylene," as used herein, refers to a divalent group of two to eight atoms derived from a saturated straight or branched chain containing one or two heteroatoms independently selected from nitrogen, oxygen, and sulfur, wherein the remaining atoms are carbon. The heteroalkylene groups of the present disclosure can be attached through the carbon atoms or the heteroatoms in the chain.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a phenyl group, a monocyclic cycloalkenyl group, as defined herein, a monocyclic cycloalkyl group, as defined herein, a monocyclic heterocyclyl group, as defined herein, or an additional monocyclic heteroaryl group; and tricyclic systems where a bicyclic system is fused to a phenyl group, a monocyclic cycloalkenyl group, as defined herein, a monocyclic cycloalkyl group, as defined herein, a heterocyclyl group, as defined herein, or an additional monocyclic heteroaryl group. The heteroaryl groups are attached to the parent molecular moiety through any substitutable carbon or nitrogen atom in the group. Representative examples of heteroaryl groups include, but are not limited to, benzoxadiazolyl, benzoxazolyl, benzofuranyl, benzothienyl, cinnolinyl, dibenzofuranyl, furanyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl. The heteroaryl groups of the present disclosure can be optionally substituted with one, two, three, four, or five substituents independently selected from alkenyl, alkoxy, alkyl, halo, haloalkoxy, haloalkyl, hydroxy, and oxo.

The term "heteroarylalkyl," as used herein, refers to an alkyl group substituted with one, two, or three heteroaryl groups.

The term "heterocyclyl," as used herein, refers to a cyclic, non-aromatic, saturated or partially unsaturated three-, four-, five-, six-, or seven-membered ring where at least one atom is selected from oxygen, nitrogen, and sulfur. The term "heterocyclyl" also includes bicyclic systems where a heterocyclyl ring is fused to a phenyl group, a monocyclic cycloalkenyl group, a monocyclic cycloalkyl group, or an additional monocyclic heterocyclyl group; and tricyclic systems where a bicyclic system is fused to a phenyl group, a monocyclic cycloalkenyl group, a monocyclic cycloalkyl group, or an additional monocyclic heterocyclyl group. The heterocyclyl groups of the disclosure are attached to the parent molecular group through any substitutable carbon or nitrogen atom in the group. Representative examples of heterocyclyl groups include, but are not limited to, benzodioxolyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, and thiomorpholinyl. The heterocyclyl groups of the present disclosure can be optionally substituted with one, two, three, four, or five substituents independently selected from alkenyl, alkoxy, alkyl, halo, haloalkoxy, haloalkyl, hydroxy, and oxo.

The term "heterocyclylalkyl," as used herein, refers to an alkyl group substituted with one, two, or three heterocyclyl groups.

The term "hydroxy," as used herein, refers to —OH.

The term "—NR$^a$R$^b$," as used herein, refers to two groups, R$^a$ and R$^b$, which are attached to the parent molecular moiety through a nitrogen atom. R$^a$ and R$^b$ are independently selected from hydrogen, alkyl, aryl, and arylalkyl.

The term "oxo," as used herein, refers to =O.

The term "spirocycle," as used herein, refers to an alkenylene, alkylene, heteroalkenylene, or heteroalkylene diradical wherein both ends of the diradical are attached to the same carbon atom of the parent molecular moiety forming a 3- to 8-membered saturated or partially unsaturated ring. The ring can be optionally fused to a 5- to 7-membered aromatic or non-aromatic carbocyclic, heteroaromatic, or heterocyclic ring to form a bicyclic spirocycle.

The term "thiooxo," as used herein, refers to =S.

The term "trialkylsilyl," as used herein, refers to —SiR$_3$ wherein R is alkyl. Each R may be the same or may be a different alkyl group.

The term "compounds of the disclosure", and equivalent expressions, are meant to embrace compounds of formula (I), and pharmaceutically acceptable enantiomers, diastereomers, salts, and solvates, e.g. hydrates, thereof. Similarly, references to intermediates are meant to embrace their salts and solvates where the context so permits. The term "solvate" means a physical association of a compound of this disclosure with one or more solvent molecules, whether organic or inorganic. This physical association includes hydrogen bonding. In certain instances the solvate will be capable of isolation, for example when one or more solvent molecules are incorporated in the crystal lattice of the crystalline solid. The term "solvate" encompasses both solution-phase and isolable solvates. Exemplary solvates include hydrates, ethanolates, methanolates, and the like.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgement, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, acistrate, adipate, alginate, aspartate, benzenesulfonate, benzoate, bicarbonate, bisulfate, bitartrate, bromide, butyrate, camphorsulfonate, carbonate, chloride, citrate, calcium edetate, dihydrochloride, diphosphate, edetate, edisylate, estolate, esylate, formate, fumarate, gluceptate, gluconate, glucuronate, glutamate, glycerophosphate, glycollylarsanilate, hemisulfate, heptanoate, hexanoate, hexylresorcinate, hippurate, hyclate, hydrabamine, hydrobromide, hydrochloride, hydroiodide, 2-hydroxyethanesulfonate, hydroxynaphthoate, iodide, lactate, lactobionate, malate, maleate, mandelate, mesitylenesulfonate, methanesulfonate, methylbromide, methylnitrate, methylsulfate, mucate, naphthylenesulfonate, 2-naphthalenesulfonate, nicotinate, nitrate, oleate, oxalate, pamoate, pantothenate, pectinate, persulfate, 3-phenylproprionate, phosphate, picrate, pivalate, polygalacturonate, propionate, salicylate, stearate, subacetate, succinate, sulfate, sulfosalicylate, tannate, tartrate, teoclate, terephthlate, para-toluenesulfonate, trichloroacetate, triethiodide, trifluoroacetate, undecanoate, and xinafoate.

Basic addition salts can be prepared during the final isolation and purification of the compounds by reacting an acidic proton with a suitable base such as the hydroxide, carbonate, or bicarbonate of a metal cation or with ammonia or an organic primary, secondary, or tertiary amine. The cations of pharmaceutically acceptable salts include alkali metals (e.g., sodium and potassium), alkaline earth metals (e.g., calcium and magnesium), aluminum, zinc, ammonium tetramethylammonium, and tetraethylammonium. In addition, suitable base addition salts include salts of physiologically acceptable organic bases such as chloroprocaine, choline, dibenzylamine, N,N'-dibenzylethylenediamine, N,N-dibenzylphenethylamine, dicyclohexylamine, diethanolamine, diethylamine, dimethylamine, N,N-dimethylaniline, diolamine, ethanolamine, ethylamine, ethylenediamine, meglumine, methylamine, N-methylmorpholine, N-methylpiperidine, olamine, 4-phenylcyclohexylamine, piperazine, piperidine, procaine, pyridine, tributylamine, triethylamine, trimethylamine, and tromethamine.

Certain compounds of formula (I) may contain one or more chiral centers and exist in different optically active forms. It should be understood that the present disclosure encompasses all stereochemical isomeric forms, or mixtures thereof, which possess the ability to inhibit HIV integrase. When compounds of formula (I) contain one chiral center, the compounds exist in two enantiomeric forms. The enantiomers may be resolved by methods known to those skilled in the art, for example, by formation of diastereoisomeric salts which may be separated by crystallization, gas-liquid, or liquid chromatography; or by selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts, or solvents, or by converting one enantiomer into the other by asymmetric transformation. Starting compounds of particular stereochemistry are either commercially available or can be made and resolved by techniques known in the art.

The compounds of the present disclosure can exist as tautomers, as shown below. The present disclosure encompasses all tautomeric forms.

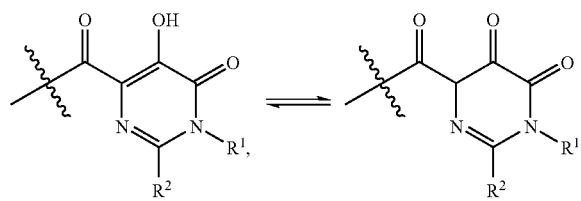

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgement, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 1 to 1000 millograms per kilogram ("mg/kg") body weight per day, for example, between about 1 and about 200 mg/kg body weight per day of the compounds of the disclosure are typical in a monotherapy for the prevention and treatment of HIV. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. In one embodiment, unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, for example, between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection two specific methods of administration contemplated by the present disclosure.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3, 318.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations can be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human(s) and other mammals.

The term "treating" refers to: (i) preventing a disease, disorder or condition from occurring in a patient that has not yet been diagnosed as having it; (ii) inhibiting the disease, disorder, or condition, i.e., arresting its development; and (iii) relieving the disease, disorder, or condition, i.e., causing regression of the disease, disorder, and/or condition.

While the compounds of the disclosure can be administered as the sole active pharmaceutical agent, they can also be used in combination with one or more immunomodulators, antiviral agents, other antiinfective agents, or vaccines. Tables 1–3 below lists some illustrative examples of compounds that can be administered with the compounds of this disclosure. The compounds of the disclosure can be administered with other treatments for HIV in combination therapy, either jointly or separately, or by combining the compounds into a composition.

TABLE 1

| ANTIVIRALS | | |
|---|---|---|
| Drug Name | Manufacturer | Indication |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |

TABLE 1-continued

| ANTIVIRALS | | |
|---|---|---|
| Drug Name | Manufacturer | Indication |
| BMS-232623 (CGP-73547) (protease inhibitor) | Bristol-Myers Squibb/Novartis | HIV infection, AIDS, ARC |
| BMS-234475 (CGP-61755) (protease inhibitor) | Bristol-Myers Squibb/Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase | Glaxo Wellcome | HIV infection, AIDS, ARC, |

TABLE 1-continued

ANTIVIRALS

| Drug Name | Manufacturer | Indication |
|---|---|---|
| inhibitor) | | also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succiante (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |

TABLE 2

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/ TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immuno-therapeutic |
| rCD4 Recombinant Soluble Human CD4 | Genentech | AIDS, ARC |
| rCD4-IgG hybrids | | AIDS, ARC |

TABLE 2-continued

IMMUNOMODULATORS

| Drug Name | Manufacturer | Indication |
| --- | --- | --- |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

TABLE 3

ANTI-INFECTIVES

| Drug Name | Manufacturer | Indication |
| --- | --- | --- |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Dannorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. with AIDS |
| Testosterone | Alza, Smith Kline | AIDS-related wasting |
| Total Enteral Nutrition | Norwich Eaton Pharmaceuticals | Diarrhea and malabsorption related to AIDS |

The compounds and processes of the present disclosure will be better understood in connection with the following synthetic schemes which illustrate the methods by which the compounds of the disclosure may be prepared. The following methods set forth below are provided for illustrative purposes and are not intended to limit the scope of the present disclosure. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of $R^1$–$R^4$, $R^7$, $R^8$, $R^a$, and $R^b$ to successfully complete the syntheses below. The groups $R^1$–$R^4$, $R^7$, $R^8$, $R^a$, and $R^b$ are as defined above unless otherwise noted below.

Abbreviations used within the schemes and examples are as follows: DMF for N,N-dimethylformamide; THF for tetrahydrofuran; TFA for trifluoroacetic acid; and DMSO for dimethylsulfoxide.

This disclosure is intended to encompass compounds having formula (I) when prepared by synthetic processes or by metabolic processes. Preparation of the compounds of the disclosure by metabolic processes include those occurring in the human or animal body (in vivo) or processes occurring in vitro.

The compounds of the present disclosure can be manufactured by methods known to those skilled in the art, (see, for example, *Inorg. Chem.* 2001, 40, 6756–6756). In Scheme I, an oxalic acid diester 1-1 is condensed with glycolate 1-2 using sodium hydride or a similar base. The intermediate generated from this reaction can be isolated but more often is reacted in one pot with an appropriately substituted amidine (1-3) to yield the pyrimidinone heterocycle 1-4. This is alkylated with a suitable electrophile, 1-5, under basic conditions. From here there are two pathways to the final product. In one path intermediate 1-6 is treated with base to saponify the ester and the resulting acid is coupled with amine 1-7. It will be appreciated by those skilled in the art that the amide coupling reaction can be carried out under a variety of conditions such as those disclosed March, *Advanced Organic Chemistry*, 3$^{rd}$ edition, John Wiley & Sons, 1985. The resulting amide, 1-8 is then treated under conditions appropriate for cleaving the protecting group $R_y$, to yield 1-10. Where $R_y$ is alkyl, this can be accomplished by $BBr_3$ or other conditions familiar to those skilled in the art, such as treatment with LiI. Alternatively, when $R_y$ is a benzylic or substituted benzylic group the ether can be cleaved under reductive conditions, oxidative conditions or acidic conditions. Protecting groups, such as $R_x$ $R_y$, and $R_z$, useful for the synthesis of compounds such as 1-9 can be found in Greene, T. W. and Wutz, P. G. M. *Protective Groups in Organic Synthesis*, Second Edition, 1991, John Wiley and Sons, New York. In the alternative pathway, the protecting group is removed from 1-6 to yield 1-9. At elevated temperatures 1-9 reacts with amines (1-7) to afford 1-10.

Scheme I

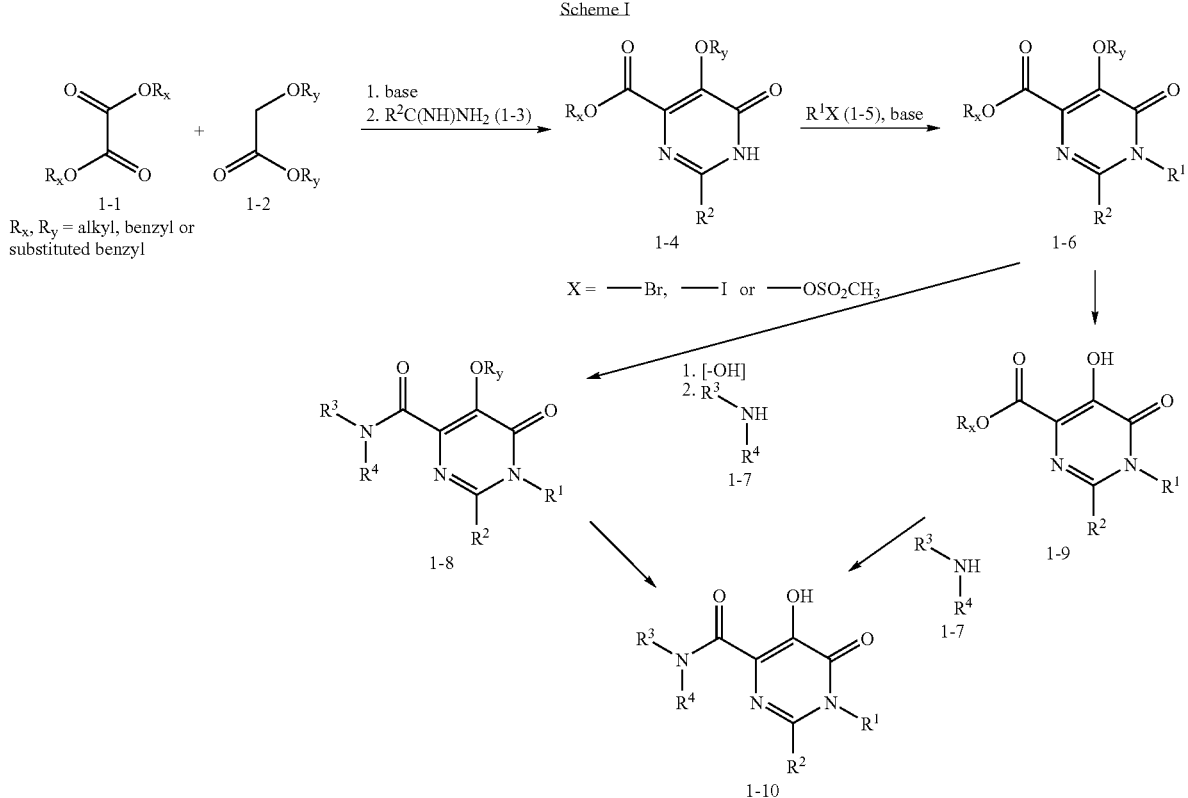

In Scheme II, an alternative pathway is shown in which the $R^2$ group is introduced at a later stage of the synthesis. Thus, 2-2 is formed from an oxalate ester, protected glycolic acid, and S-methylthiourea using the same conditions as described in Scheme I. This intermediate is alkylated under the conditions described in Scheme I and optionally oxidized to yield 2-4. The thiomethyll group is then displaced with a nitrogen containing heterocycle, such as those shown in the scheme, under acidic conditions (HCl) similar to those described in *J. Heterocycic Chem.* 1997, 34, 551–556, for example, or after oxidation of the sulfur atom as described in *Bioorg. Med. Chem. Lett.* 1995, 23, 2879–2884. Following the installation of the amine at C-2 of the pyrimidine template there are two pathways for introducing the amide group. These are essentially the same as those described in Scheme I.

Scheme II

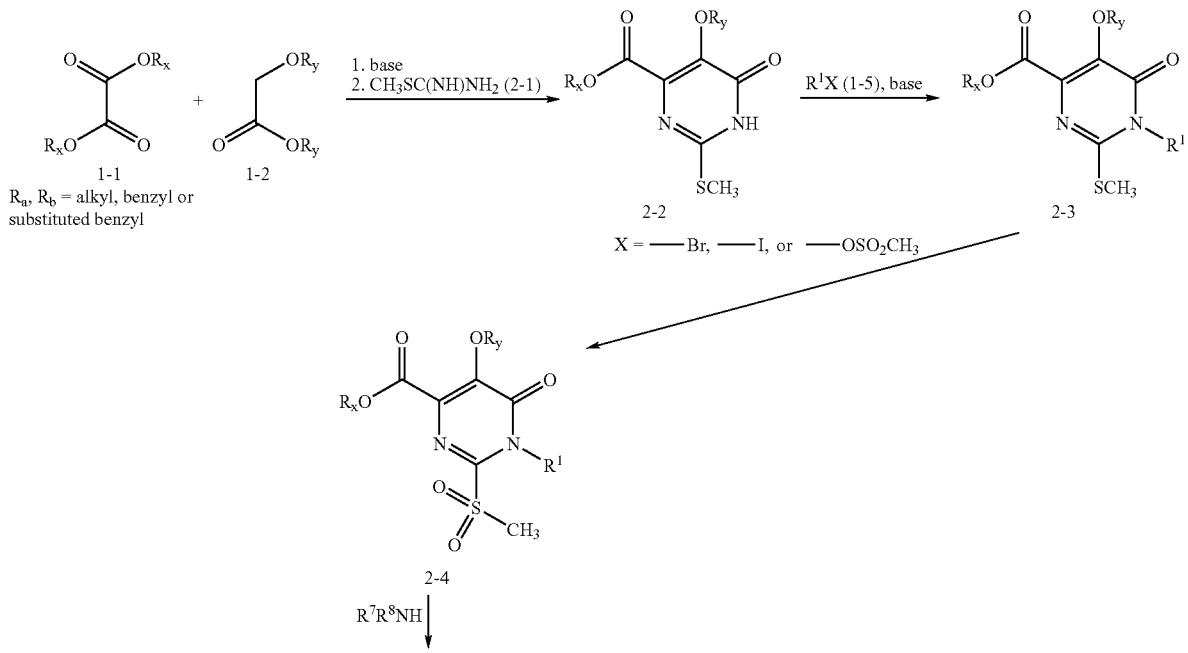

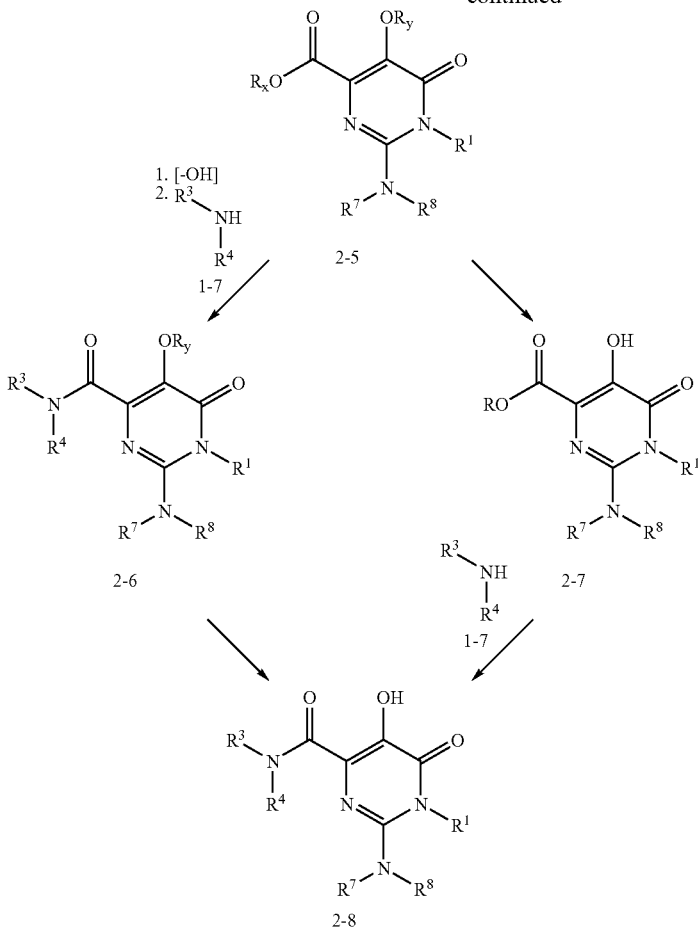

An alternative route to intermediate 2-3 is shown in Scheme III. Methylthiocyanate reacts with appropriately substituted amines to form N-hydroxyl amidines such as 3-2. This intermediate will react with an alkyne-diester to afford a mixture of 3-4 and 3-5. Both of these compounds will rearrange to form the hydroxypyrimidinone template (*J. Heterocyclic Chem.* 1979, 16, 1423–1424). Reaction with an appropriate electrophile results in 2-3.

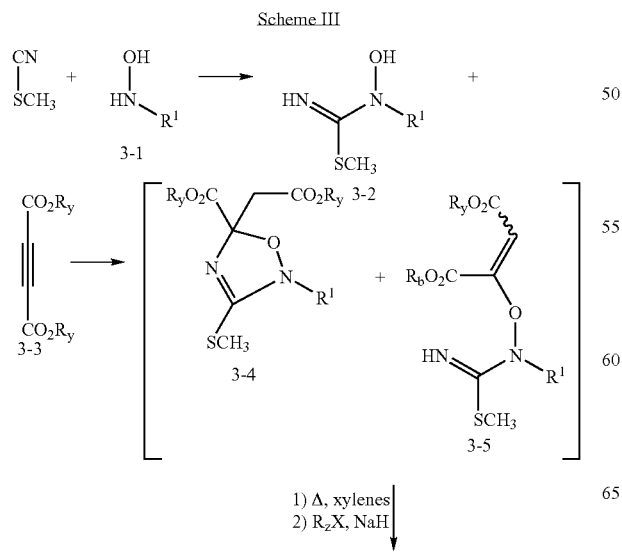

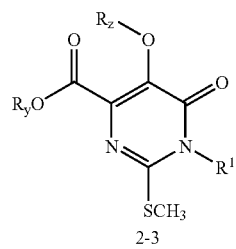

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

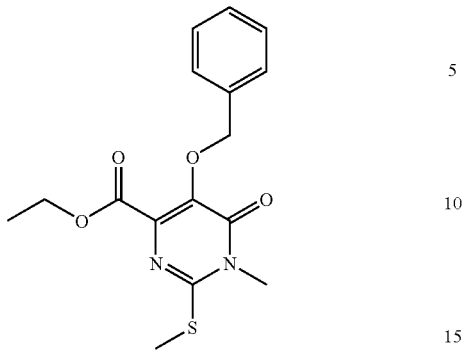

2-methanesulfonyl-1,6-dihydro-1-methyl-6-oxo-5-(phenylmethoxy)-4-pyrimidinecarboxylic acid, ethyl ester A stirred solution of methylthiocyanate (91 g, 1.245 mol) and N-methylhydroxylamine hydrochloride (100 g, 1.197 mol) in 1:1 ethanol/water (v/v, 500 mL) was carefully treated with $Na_2CO_3$ (63.6 g, 0.6 mol) over 30 minutes at room temperature. The resulting reaction mixture was stirred 48 hours then cooled in an ice-water bath. The mixture was slowly treated with diethyl acetylenedicarboxylate (192 mL, 1.2 mol) over 10 minutes. After stirring 2 hours, the resulting dark-brown reaction mixture was transferred to a separatory funnel and extracted with ethyl acetate (3×250 mL). The combined organic layers were dried ($Na_2SO_4$/activated charcoal), filtered, and concentrated to give a dark-brown residue (310.1 g) which was used in the next step without further purification.

A solution of the above crude intermediate in xylenes (1.2 L) was placed in a pre-heated oil bath (140° C.) and stirred for 48 hours. The mixture was then cooled and concentrated to give a dark solid. This crude product mixture was dissolved in anhydrous DMF (1.5 L), treated with benzyl bromide (119 mL, 1 mol) and $K_2CO_3$ (138 g, 1 mol). After stirring for 72 hours at room temperature, the reaction mixture was diluted with hexanes (1 L) and filtered. The filtrate was concentrated under vacuum and the resulting residue was dissolved in diethyl ether (1 L), washed with water (3×250 mL) and brine (200 mL), dried ($Na_2SO_4$/activated charcoal), filtered and concentrated to afford dark paste which was dissolved in diethyl ether/hexanes (2:1, 1.5 L). Approximately 1 L of the solvent was removed on a rotary evaporator. The resulting solution was left overnight at room temperature and the brown-crystals which formed were removed by filtration. The filtrate was concentrated then purified by chromatography (EM Science silica gel 60, column size ~30×10 $cm^2$) using 8:1:1 hexanes/ethyl acetate/$CH_2Cl_2$ solvent system and collected in 250 mL fractions. The fractions containing the desired compound were combined and concentrated to give a viscous oil which was dissolved in hexanes/diethyl ether (~4:1) and allowed to crystallize (92.3 g). The desired product was collected by filtration. The filtrate was concentrated and allowed to sit at room temperature for 48 hours to provide an additional 8.84 g of the desired product. Total yield: 101.14 g (25.3%). mp 84–85° C. $^1$H NMR (400 MHz, $CDCl_3$) δ 1.33 (3H, t, J=7.0 Hz), 2.62 (3H, s), 3.57 (3H, s), 4.35 (2H, q, J=7.0 Hz), 5.22 (2H, s), 7.3–7.5 (5H, m). Anal. calcd for $C_{16}H_{18}N_2O_4S$: C, 57.47; H, 5.43; N, 8.38. Found: C, 57.37; H, 5.42; N, 8.36.

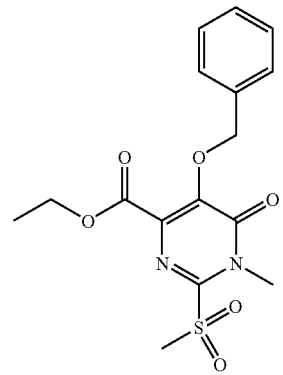

Intermediate 1B

2-methanesulfonyl-1,6-dihydro-1-methyl-6-oxo-5-(phenylmethoxy)-4-pyrimidinecarboxylic acid, ethyl ester A mixture of Intermediate 1A (5.83 g, 17.43 mmol) in dry dichloromethane (250 mL) was treated with 3-chloroperoxybenzoic acid (12.5 g of 85%, 61.6 mmol) and stirred at room temp for 2 hours. The mixture was washed with aqueous 10% sodium bisulfite (2×50 mL), saturated aqueous sodium bicarbonate (4×50 mL), and brine, dried ($Na_2SO_4$), filtered, concentrated and purified by chromatography on silica gel with 0–25% ethyl acetate in hexane to provide 5.27 g (82% yield) of the desired product as a white solid; mp 65–67° C. $^1$HNMR 400 MHz ($CDCl_3$) δ 1.30 (3H, t, J=7.1 Hz), 3.45 (3H, s), 3.87 (3H, s), 4.32 (2H, q, J=7.1 Hz), 5.42 (2H, s), 7.3–7.5 (5H, m). Anal. calcd for $C_{16}H_{18}N_2O_6S$: C, 52.45; H, 4.95; N, 7.65. Found: C, 52.27; H, 4.69; N, 7.58.

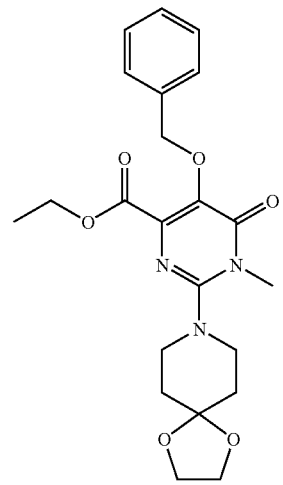

Intermediate 1C

2-(1,4-dioxa-8-azaspiro[4.5]dec-8-yl)-1,6-dihydro-1-methyl-6-oxo-5-(phenylmethoxy)-4-pyrimidinecarboxylic acid, ethyl ester To a solution of Intermediate 1B (0.40 g, 1.10 mmol) dissolved in THF (2 mL) was added 1,4-dioxa-8-azaspiro

[4,5]decane (0.35 mL, 2.7 mmol). The resulting mixture was stirred at 70° C. for 1.5 hours. The mixture was concentrated and the resulting residue was purified by flash chromatography eluting with 0% to 40% ethyl acetate/hexane to provide the desired product as a pale yellow solid (0.3146 g, 67% yield). $^1$H NMR (300 MHz, CDCl$_3$) δ 7.49–7.45 (2H, m), 7.37–7.29 (3H, m), 5.14 (2H, s), 4.30 (2H, q, J=7.2 Hz), 3.97 (4H, s), 3.50 (3, s), 3.30–3.27 (4H, m), 1.84–1.81 (4H, m), 1.28 (3H, t, J=7.1 Hz). HRMS (M+H) calcd. for C$_{22}$H$_{28}$N$_3$O$_6$: 430.19782; found: 430.1996.

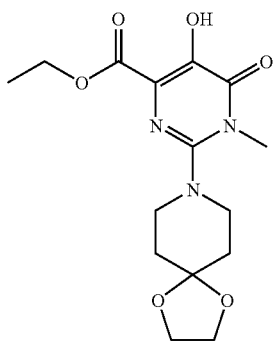

Intermediate 1D 2-(1,4-dioxa-8-azaspiro[4.5]dec-8-yl)-1,6-dihydro-5-hydroxy-1-methyl-6-oxo-4-pyrimidinecarboxylic acid, ethyl ester To a solution of Intermediate 1C (0.31 g, 0.72 mmol) in ethanol (20 mL) was added palladium on carbon (0.03 g). The resulting suspension was shaken under H$_2$ at 50 psi for 4 hours, filtered through diatomaceous earth (Celite®), and concentrated to provide the desired product as a white solid (0.2135 g, 87% yield). $^1$H NMR (500 MHz, CDCl$_3$) δ 10.21 (1H, s), 4.42 (2H, q, J=7.1 Hz), 3.99 (4H, s), 3.53 ((3H, s), 3.22–3.20 (4H, m), 1.86–1.84 (4H, m), 1.42 (3H, t, J=7.2 Hz). HRMS (M+H) calcd. for C$_{15}$H$_{22}$N$_3$O$_6$: 340.15087; found: 340.1514.

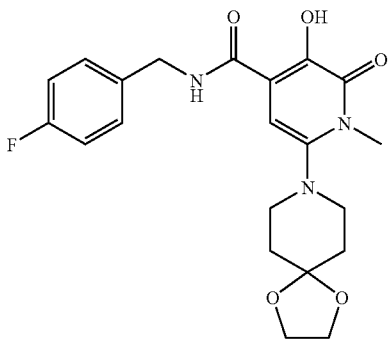

EXAMPLE 1

2-(1,4-dioxa-8-azaspiro[4.5]dec-8-yl)-N-[(4-fluorophenyl)methyl]-1,6-dihydro-5-hydroxy-1-methyl-6-oxo-4-pyrimidinecarboxamide To a solution of Intermediate 1D (0.068 g, 0.2 mmol) in 1:1 ethanol/DMF (1 mL) was added triethylamine (0.056 mL, 0.4 mmol) followed by 4-fluorobenzylamine (0.065 mL, 0.5 mmol). The mixture was stirred at 100° C. for 1 hour. After cooling to room temperature, the white solids were filtered and dissolved in DMF and purified by chromatography (YMC Combiprep ODS-A, 30 mm×50 mm, methanol/H$_2$O/0.1% TFA) to provide the desired product as a white solid (0.0185 g, 22% yield). $^1$H NMR (300 MHz, CD$_3$OD) δ 8.77 (1H, br s), 7.36 (2H, dd, J=8.4, 5.5 Hz), 7.05 (2H, t, J=8.6 Hz), 4.54 (2H, d, J=3.7 Hz), 3.97 (4H, s), 3.53 (3H, s), 3.23–3.19 (4H, m), 1.85–1.82 (4H, m). HRMS (M+H) calcd. for C$_{20}$H$_{24}$N$_4$O$_5$F: 419.17308; found: 419.1746.

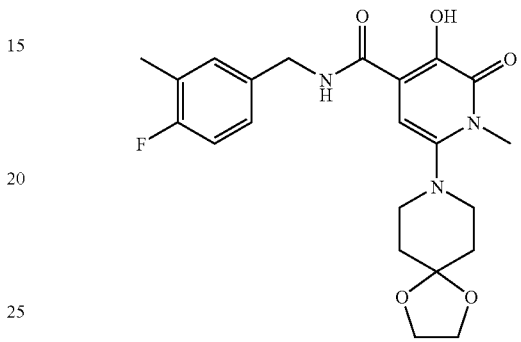

EXAMPLE 2

2-(1,4-dioxa-8-azaspiro[4,5]dec-8-yl)-N-[(4-fluoro-3-methylphenyl)methyl]-1,6-dihydro-5-hydroxy-1-methyl-6-oxo-4-pyrimidinecarboxamide The desired product was prepared following the procedure of Example 1 from Example 1D (0.068 g, 0.2 mmol), triethylamine (0.056 mL, 0.4 mmol), 3-methyl-4-fluorobenzylamine (0.067 mL, 0.5 mmol), followed by purifying the crude reaction mixture by chromatography (YMC Combiprep ODS-A, 30 mm×50 mm, CH$_3$OH/H$_2$O/0.1% TFA) to provide the desired product as a white solid (0.429 g, 50% yield). $^1$H NMR (300 MHz, CDCl$_3$) δ 11.66 (1H, br s), 7.77–7.73 (1H, m), 7.14–7.08 (2H, m), 6.97 (1H, t, J=8.8 Hz), 4.51 (2H, d, J=6.2 Hz), 3.98 (4H, s), 3.53 (3H, s), 3.14–3.10 (4H, m), 2.27 (3H, s), 1.85–1.81 (4H, m). HRMS (M+H) calcd. for C$_{21}$H$_{26}$N$_4$O$_5$F: 433.18873; found: 433.1891. Anal. calcd for C$_{23}$H$_{25}$N$_4$O$_3$F: C, 58.33; H, 5.83; N, 12.96; F, 4.39; found: C, 58.10; H, 5.70; N, 12.64; F, 4.70.

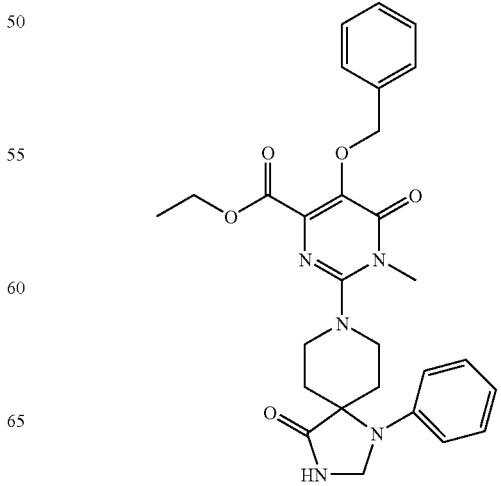

Intermediate 3A 1,6-dihydro-1-methyl-6-oxo-2-(4-oxo-1-phenyl-1,3,8-triazaspiro[4,5]dec-8-yl)-5-(phenylmethoxy)-4-pyrimidinecarboxylic acid, ethyl ester To a solution of Intermediate 1B (0.80 g, 2.18 mmol) dissolved in THF (8 mL) was added 1-phenyl-1,3,8-triazaspiro[4,5]decane-4-one (2.50 g, 10.9 mmol).

The resulting mixture was stirred at 90° C. for 1.5 hours. The mixture was cooled to room temperature, filtered, and concentrated and the resulting residue was purified by flash chromatography eluting with 0%–25%–50%–100% ethyl acetate/hexane to provide the desired product as a white solid (0.4759 g, 42% yield). $^1$H NMR (300 MHz, CDCl$_3$) δ 7.51 (2H, d, J=7.0 Hz), 7.37 (2H, t, J=7.3 Hz), 7.34–7.31 (1H, m), 7.28–7.25 (2H, m), 6.88–6.82 (3H, m), 6.40 (1H, s), 5.20 (2H, s), 4.78 (2H, s), 4.32 (2H, q, J=7.1 Hz), 3.84 (2H, td, J=13.1, 3.0 Hz), 3.58–3.55 (2H, m), 3.55 (3H, s), 2.89 (2H, td, J=13.4, 5.3 Hz), 1.75 (2H, d, J=14.3 Hz), 1.28 (3H, t, J=7.4 Hz). HRMS (M+H) calcd. for C$_{28}$H$_{32}$N$_5$O$_5$: 518.24035; found: 518.2400.

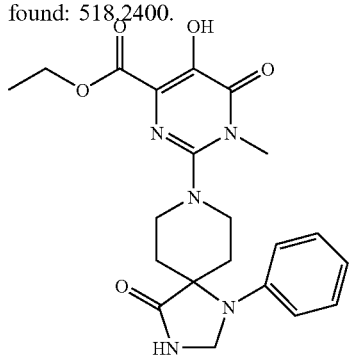

Intermediate 3B 1,6-dihydro-5-hydroxy-1-methyl-6-oxo-2-(4-oxo-1-phenyl-1,3,8-triazaspiro[4.5]dec-8-yl)-4-pyrimidinecarboxylic acid, ethyl ester The desired product was prepared following the procedure of Intermediate 1D from Intermediate 3A using a solution of ethanol/methanol (1:1) to give desired product as a white solid (0.0835 g, 21% yield). $^1$H NMR (300 MHz, CDCl$_3$) δ 10.32 (1H, s), 7.17 (2H, t, J=7.9 Hz), 6.83–6.78 (3H, m), 6.24 (1H, s), 4.75 (2H, s), 4.38 (2H, t, J=7.1 Hz), 3.77 (2H, td, J=12.6, 2.1 Hz), 3.54 (3H, s), 3.43–3.37 (2H, m), 2.91 (2H, td, J=13.4, 5.1 Hz), 1.69 (2H, d, J=15.4 Hz), 1.30 (3H, t, J=6.9 Hz).

EXAMPLE 3

N-[(4-fluorophenyl)methyl]-1,6-dihydro-5-hydroxy-1-methyl-6-oxo-2-(4-oxo-1-phenyl-1,3,8-triazaspiro[4.5]dec-8-yl)-4-pyrimidinecarboxamide A solution of Intermediate 3B (0.04 g, 0.09 mmol) dissolved in 1-methyl-2-pyrrolidinone (2 mL) was treated with 4-fluorobenzylamine (0.065 mL, 0.5 mmol) and the mixture was stirred at 75° C. for 4 hours. The solution was cooled to room temperature and purified by chromatography (YMC Combiprep ODS-A, 30 mm×50 mm, methanol/H$_2$O/0.1% TFA) to provide the desired product as a white solid (0.019 g, 42% yield). $^1$H NMR (300 MHz, CDCl$_3$) δ 11.67 (1H, br s), 7.74 (1H, t, J=6.6 Hz), 6.97 (2H, t, J=8.6 Hz), 6.85 (2H, t, J=8.4 Hz), 4.78 (2H, s), 4.52 (2H, d, J=6.2 Hz), 3.67–3.58 (2H, m), 3.54 (3H, s), 3.34–3.28 (2H, m), 2.73 (2H, td, J=13.4, 5.4 Hz), 1.80 (2H, d, J=14.6 Hz). HRMS (M+H) calcd. for C$_{26}$H$_{28}$N$_6$O$_4$F: 507.21562; found: 507.2156. Anal. calcd for C$_{26}$H$_{27}$N$_6$O$_4$F.0.25TFA.1.5H$_2$O: C, 56.63; H, 5.42; N, 14.95; F, 5.92; found: C, 56.75; H, 5.08; N, 14.58; F, 6.14.

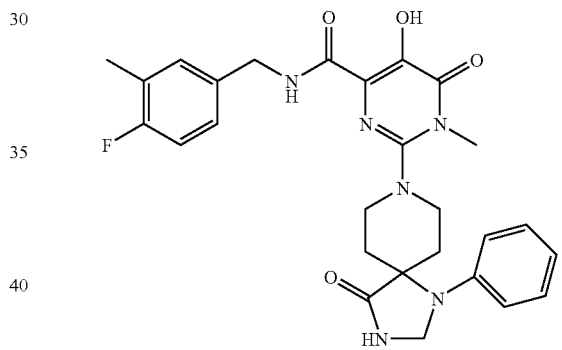

EXAMPLE 4

N-[(4-fluoro-3-methylphenyl)methyl]-1,6-dihydro-5-hydroxy-1-methyl-6-oxo-2-(4-oxo-1-phenyl-1,3,8-triazaspiro[4.5]dec-8-yl)-4-pyrimidinecarboxamide The desired product was prepared following the procedure of Example 3 from Intermediate 3B and 3-methyl-4-fluorobenzylamine (0.067 mL, 0.5 mmol) to give the desired product as a white solid (0.016 g, 35% yield). $^1$H NMR (300 MHz, CDCl$_3$) δ 11.68 (1H, br s), 7.72 (1H, br s), 7.07–7.04 (1H, m), 6.87 (2H, dd, J=12.6, 7.9 Hz), 4.77 (2H, s), 4.96 (2H, d, J=6.2 Hz), 3.64 (2H, t, J=12.6 Hz), 3.54 (3H, s), 3.34–3.29 (2H, m), 2.78–2.69 (1H, m), 2.20 (3H, s), 1.79 (2H, d, J=13.9 Hz). HRMS (M+H) calcd. for C$_{27}$H$_{30}$N$_6$O$_4$F: 521.23127; found: 521.2323. Anal. calcd for C$_{27}$H$_{29}$N$_6$O$_4$F.0.05TFA.0.5H$_2$O: C, 60.81; H, 5.66; N, 15.70; F, 4.08; found: C, 60.79; H, 5.51; N, 15.60; F, 4.15.

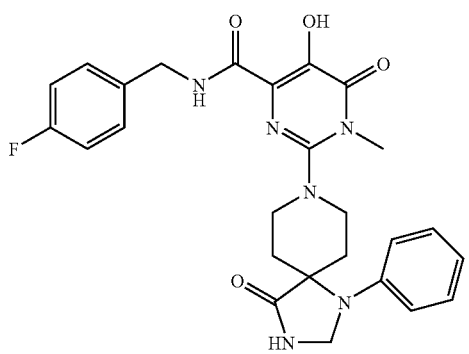

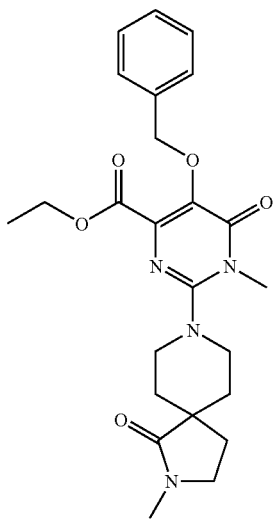

Intermediate 5A 1,6-dihydro-1-methyl-2-(2-methyl-1-oxo-2,8-diazaspiro[4.5]dec-8-yl)-6-oxo-5-(phenylmethoxy)-4-pyrimidinecarboxylic acid ethyl ester To a solution of Intermediate 1B (0.0.366 g, 1 mmol) in THF (4 mL) was added a suspension of 2-methyl-2,8-diazaspiro[4.5]decan-1-one hydrochloride (0.20 g, 1 mmol) in triethylamine (1 mL) in THF (2 mL). The resulting mixture was stirred at 80° C. for 2 hours. The mixture was cooled to room temperature and concentrated and the resulting residue was purified by flash chromatography eluting with 0%–50% ethyl acetate/hexane followed by 1%–2% methanol/$CH_2Cl_2$ to provide the desired product as a yellow solid (0.111 g, 24% yield). $^1$H NMR (500 MHz, $CDCl_3$) δ 7.48 (2H, d, J=7.0 Hz), 7.37–7.29 (3H, m), 5.17 (2H, s), 4.31 (2H, q, J=7.1 Hz), 3.54 (3H, s), 3.46 (2H, d, J=13.4 Hz), 3.34 (2H, t, J=6.9 Hz), 2.96 (2H, t, J=11.7 Hz), 2.88 (3H, s), 2.08 (2H, td, J=12.8, 3.6 Hz), 2.00 (2H, t, J=7.0 Hz), 1.53 (2H, J=13.4 Hz), 1.30 (3H, t, J=7.2 Hz). HRMS (M+H) calcd. for $C_{24}H_{31}N_4O_5$: 455.22162; found: 455.2309.

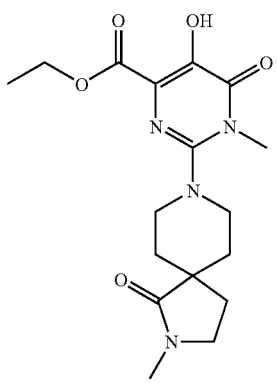

Intermediate 5B 1,6-dihydro-5-hydroxy-1-methyl-2-(2-methyl-1-oxo-2,8-diazaspiro[4.5]dec-8-yl)-6-oxo-4-pyrimidinecarboxylic acid ethyl ester A mixture of Intermediate 5A (0.10 g, 0.22 mmol) in TFA (2 mL) was stirred at room temperature for 24 hours and concentrated to give the desired product as a brown oil that was used directly without further purification. $^1$H NMR (300 MHz, $CDCl_3$) δ 10.64 (1H, s), 4.43 (2H, q, J=7.1 Hz), 3.57 (3H, s), 3.47–3.40 (4H, m), 3.04 (2H, t, J=12.2 Hz), 2.92 (3H, s), 2.15–2.05 (4H, m), 1.56 (2H, d, J=13.2 Hz), 1.38 (3H, t, J=6.9 Hz). LCMS (M+H) calcd. for $C_{17}H_{25}N_4O_5$: 365.17; found 365.36.

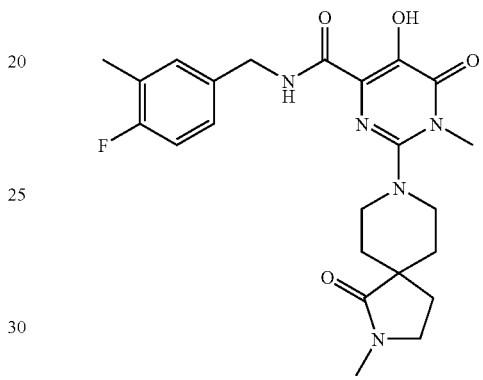

EXAMPLE 5

N-[(4-fluoro-3-methylphenyl)methyl]-1,6-dihydro-5-hydroxy-1-methyl-2-(2-methyl-1-oxo-2,8-diazaspiro[4.5]dec-8-yl)-6-oxo-4-pyrimidinecarboxamide The desired product was prepared following the procedure for Example 3 from Intermediate 5B (approximately 0.2 mmol) and 3-methyl-4-fluorobenzylamine (0.30 mL, 2.2 mmol) to provide the desired product as a white solid (0.030 g, 30% yield). $^1$H NMR (500 MHz, $CDCl_3$) δ: 7.80 (1H, t, J=5.8 Hz), 7.15 (1H, d, J=7.3 Hz), 7.12–7.10 (1H, m), 6.98 (1H, t, J=9.0 Hz), 4.53 (2H, d, J=6.4 Hz), 3.53 (3H, s), 3.63–3.32 (4H, m), 2.88–2.84 (2H, m), 2.86 (3H, s), 2.27 (3H, s), 2.08–2.03 (2H, m), 1.98 (2H, t, J=6.9 Hz), 1.52 (2H, d, J=13.7 Hz). HRMS (M+H) calcd. for $C_{23}H_{29}N_5O_4F$: 458.5040; found: 458.2208. Anal. calcd for $C_{23}H_{28}N_5O_4F \cdot 0.3H_2O$: C, 59.68; H, 6.23; N, 15.13; F, 4.10; found: C, 59.52; H, 5.98; N, 14.85; F, 3.88.

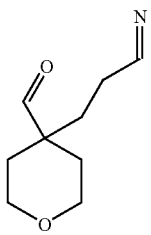

Intermediate 6A

3-(4-formyltetrahydro-2H-pyran-4-yl)propanenitrile

A solution of tetrahydro-2H-pyran-4-carbaldehyde (1.0 g, 8.77 mmol) and acrylonitrile (0.6 mL, 8.77 mmol) in dioxane (5 mL) was cooled to 0° C., treated with benzyltrimethylammonium hydroxide (0.04 mL, 40% in methanol), stirred at 0° C. for 30 minutes, warmed to room temperature, and stirred for 18 hours. The mixture was neutralized with 1N HCl and extracted with ethyl acetate. The organic phase was washed with aqueous saturated $NaHCO_3$, dried ($Na_2SO_4$), filtered, and concentrated. The oil was purified by flash chromatography eluting with 0% to 50% ethyl acetate/hexane to provide the desired product as a colorless oil (0.777 g, 53% yield).

$^1$H NMR (300 MHz, $CDCl_3$) δ 9.49 (1H, s), 3.80 (2H, dt, J=12.2, 4.1 Hz), 3.47–3.38 (2H, m), 2.22 (2H, t, J=8.0 Hz), 2.01–1.88 (4H, m), 1.60–1.51 (2H, m). LCMS (M+H) calcd. for $C_9H_{14}NO_2$: 168.10; found 168.20.

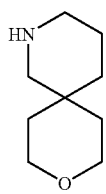

Intermediate 6B

9-oxa-2-azaspiro[5.5]undecane

A solution of Intermediate 6A (0.77 g, 4.6 mmol) dissolved in ethanol (20 mL) and 1M HCl (4.6 mL) was treated with palladium on carbon (0.01 g) and the mixture was shaken under hydrogen gas at 55 psi for 20 hours. The mixture was filtered through diatomaceous earth (Celite®) and concentrated to give a pale yellow oil that was triturated with THF. Filtration of the resulting suspension provided the desired product as a white solid (0.28 g, 32% yield). $^1$H NMR (500 MHz, $CDCl_3$) δ 9.56 (2H, br s), 3.67 (4H, t, J=5.3 Hz), 3.10 (2H, br s), 2.98 (2H, t, J=4.4 Hz), 1.90–1.84 (2H, m), 1.72–1.62 (6H, m). LCMS (M+H) calcd. for $C_9H_{18}NO$: 156.13; found 156.29.

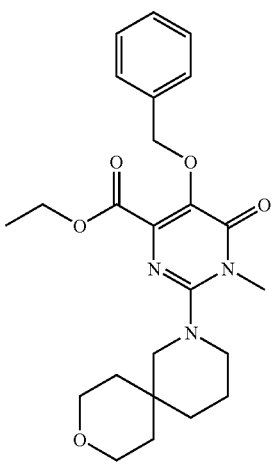

Intermediate 6C

1,6-dihydro-1-methyl-2-(3-oxa-8-azaspiro[5.5]undec-8-yl)-6-oxo-5-(phenylmethoxy)-4-pyrimidinecarboxylic acid, ethyl ester A mixture of Intermediate 1B (0.366 g, 1.0 mmol) and Intermediate 6B (1.91 g, 10 mmol) in THF (5 mL) and triethylamine (1.4 mL) was stirred at 70° C. for 8 hours. The mixture was cooled to room temperature and the solids were removed by filtration. The remaining solution was purified by chromatography (YMC Combiprep ODS-A, 30 mm×50 mm, $CH_3OH/H_2O/0.1\%$ TFA) to provide the desired product as a pale yellow oil (0.129 g, 29% yield). $^1$H NMR (300 MHz, $CDCl_3$) δ 7.46–7.42 (2H, m), 7.39–7.32 (3H, m), 5.10 (2H, s), 4.29 (2H, q, J=7.2 Hz), 3.70–3.66 (4H, m), 3.54 (3H, s), 3.13–3.09 (4H, m), 1.82–1.74 (2H, m), 1.64–1.57 (6H, m), 1.28 (3H, t, J=7.1 Hz). LCMS (M+H) calcd. for $C_{24}H_{32}N_3O_5$: 442.23; found 442.42.

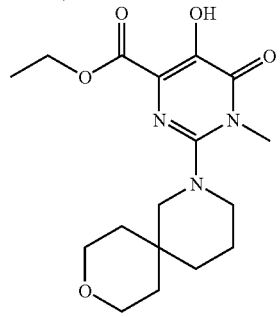

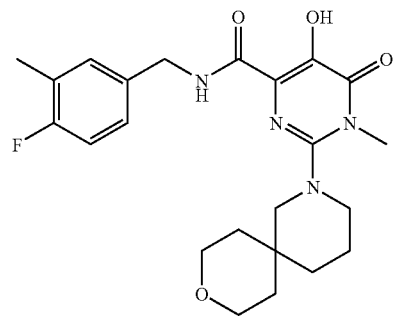

Intermediate 6D

1,6-dihydro-5-hydroxy-1-methyl-2-(3-oxa-8-azaspiro[5.5]undec-8-yl)-6-oxo-4-pyrimidinecarboxylic acid, ethyl ester The desired product was prepared following the procedure of Intermediate 5B from Intermediate 6C (0.129 g, 0.30 mmol) to provide the desired product as a brown oil that was used without further purification. $^1$H NMR (300 MHz, $CDCl_3$) δ 4.44 (2H, q, J=7.1 Hz), 3.82–3.78 (4H, m), 3.52 (3H, s), 3.07–3.02 (4H, m), 1.76–1.74 (2H, m), 1.65–1.61 (6H, m), 1.39 (3H, t, J=7.1 Hz). LCMS (M+H) calcd. for $C_{17}H_{26}N_3O_5$: 352.18; found 352.36.

EXAMPLE 6

N-[(4-fluoro-3-methylphenyl)methyl]-1,6-dihydro-5-hydroxy-1-methyl-2-(3-oxa-8-azaspiro[5.5]undec-8-yl)-6-oxo-4-pyrimidinecarboxamide The desired product was prepared following the procedure of Example 3 from Intermediate 6D (approximately 0.30 mmol) and (3-methyl-4-fluorobenzylamine (0.201 mL, 1.5 mmol) to provide the desired product as a white solid (0.079 g, 60% yield). $^1$H NMR (500 MHz, CDCl$_3$) δ11.69 (1H, br s), 7.76 (1H, t, J=5.9 Hz), 7.15 (1H, d, J=7.3 Hz), 7.13–7.10 (1H, m), 6.98 (1H, t, J=8.8 Hz), 4.55 (2H, d, J=6.4 Hz), 3.67 (4H, t, J=5.5 Hz), 3.53 (3H, s), 2.92 (2H, t, J=4.7 Hz), 2.83 (2H, s), 2.27 (3H, s), 1.76–1.71 (2H, m), 1.59–1.57 (6H, m). HRMS (M+H) calcd. for C$_{23}$H$_{30}$N$_4$O$_4$: 445.22512; found 445.2234.

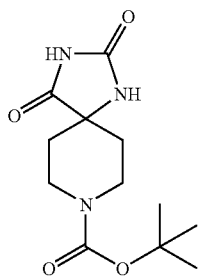

Intermediate 7A tert-butyl 2,4-dioxo-1,3,8-triazaspiro[4.5]decane-8-carboxylate A solution of tert-butyl 4-oxopiperidine-1-carboxylate (2.15 g, 10.8 mmol), in 1:1 ethanol/H$_2$O (24 mL), was treated with ammonium carbonate (1.95 g, 21.2 mmol) followed by potassium cyanide (1.30 g, 20 mmol). The mixture was stirred at 60° C. for 2 hours, cooled to room temperature, filtered, and washed sequentially with water, ethanol, and diethyl ether to provide the desired product as a white crystalline solid (1.54 g, 53% yield). $^1$H NMR (300 MHz, DMSO-d$_6$) δ 10.71 (1H, s), 8.51 (1H, s), 3.80 (2H, d, J=13.5 Hz), 3.09 (2H, br s), 1.66 (2H, td, J=12.2, 4.3 Hz), 1.53–1.46 (2H, m), 1.39 (9H, s). LCMS (2M+H) calcd. for C$_{12}$H$_{20}$N$_3$O$_4$: 539.28; found 539.41.

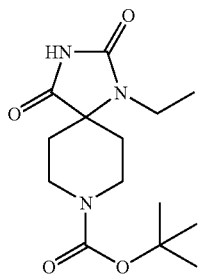

Intermediate 7B tert-butyl 1-ethyl-2,4-dioxo-1,3,8-triazaspiro[4.5]decane-8-carboxylate A solution of Intermediate 7A (1.0 g, 3.72 mmol) in DMF (15 mL), was treated with sodium hydride (0.19 g, 7.43 mmol, 95%) and stirred at 90° C. for 1.5 hours. The mixture was cooled to room temperature, treated with iodoethane (0.72 mL, 9.0 mmol), stirred at room temperature overnight, diluted with water, and extracted with ethyl acetate. The organic phase was washed with water and brine, dried (Na$_2$SO$_4$), filtered, and concentrated to provide the desired product as a white solid (0.83 g, 75% yield). $^1$H NMR (500 MHz, CDCl$_3$) δ: 6.94 (1H, s), 4.01 (2H, br s), 3.55 (2H, t, J=7.2 Hz), 3.18 (2H, t, J=10.7 Hz), 2.03–1.96 (2H, m), 1.63–1.57 (2H, m), 1.47 (9H, s), 1.20 (3H, t, J=7.2 Hz).

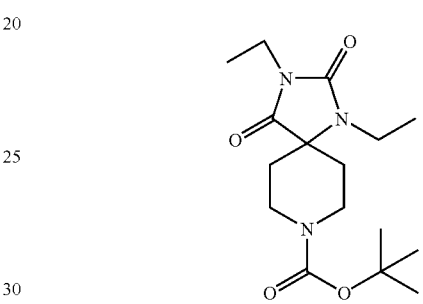

Intermediate 7C tert-butyl 1,3-diethyl-2,4-dioxo-1,3,8-triazaspiro[4.5]decane-8-carboxylate The desired product was prepared following the procedure of Intermediate 7B from Intermediate 7B (0.50 g, 1.68 mmol), sodium hydride (0.47 g, 1.85 mmol, 95%), and iodoethane (0.20 mL, 2.52 mmol) to provide the desired product as a yellow oil that was used without further purification. $^1$H NMR (300 MHz, CDCl$_3$) δ: 4.07 (2H, q, J=7.1 Hz), 3.50 (4H, q, J=7.2 Hz), 3.21 (2H, q, J=7.1 Hz), 1.83–1.73 (2H, m), 1.58 (2H, d, J=13.2 Hz), 1.43 (9H, s), 1.17 (6H, q, J=7.4 Hz). LCMS (M+H) calcd. for C$_{16}$H$_{28}$N$_3$O$_4$: 326.20; found 326.22.

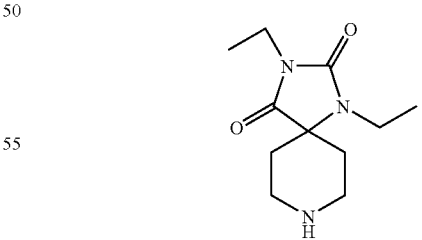

Intermediate 7D 1,3-diethyl-1,3,8-triazaspiro[4.5]decane-2,4-dione

A solution of Intermediate 7C (1.68 mmol) in TFA (6 mL) was stirred at room temperature for 3 days and concentrated.

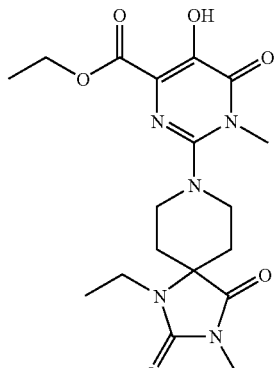

Intermediate 7F 2-(1,3-diethyl-2,4-dioxo-1,3,8-triazaspiro[4.5]dec-8-yl)-1,6-dihydro-5-hydroxy-1-methyl-6-oxo-4-pyrimidinecarboxylic acid ethyl ester The desired product was prepared following the procedure for Intermediate 5B from Intermediate 7E (0.084 g, 0.16 mmol) to provide the desired product as a brown oil that was used without further purification. LCMS (M+H) calcd. for $C_{19}H_{28}N_5O_6$: 422.20; found 422.41.

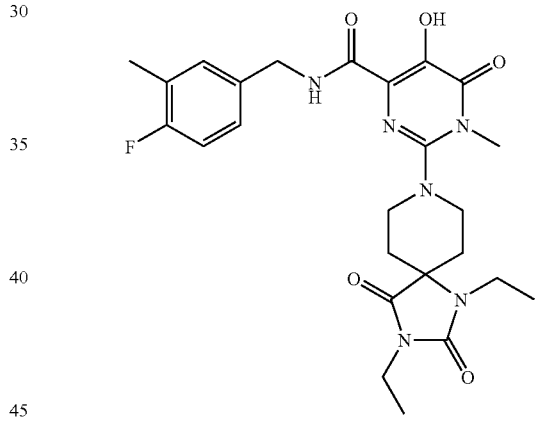

EXAMPLE 7

N-[4-fluoro-3-methylphenyl)methyl]-2-(1,3-diethyl-2,4-dioxo-1,3,8-triazaspiro[4.5]dec-8-yl)-1,6-dihydro-5-hydroxy-1-methyl-6-oxo-4-pyrimidinecarboxamide The desired product was prepared following the procedure for Example 3 from Intermediate 7F (approximately 0.16 mmol) and (3-methyl-4-fluorobenzylamine (0.11 mL, 0.8 mmol) to provide the desired product as a white solid (0.044 g, 54% yield). $^1$H NMR (300 MHz, CDCl$_3$) δ 11.73 (1H, s), 7.72 (1H, t, J=6.0 Hz), 7.13–7.06 (2H, m), 6.94 (1H, t, J=8.8 Hz), 4.50 (2H, d, J=6.6 Hz), 3.63–3.48 (4H, m), 3.52 (3H, s), 3.32–3.21 (4H, m), 2.24 (3H, d, J=1.8 Hz), 2.04 (2H, td, J=13.0, 4.3 Hz), 1.75 (2H, d, J=13.5 Hz), 1.22 (3H, t, J=7.1 Hz), 1.18 (3H, t, J=7.1 Hz). HRMS (M+H) calcd. for $C_{25}H_{32}N_6O_5F$: 515.24183; found 515.2437. Anal. calcd. for $C_{25}H_{32}N_6O_5F·0.1H_2O$: C, 58.15; H, 6.09; N, 16.28; F, 3.68; found: C, 57.84; H, 6.16; N, 15.94; F, 3.72.

The resulting colorless oil was stirred in diethyl ether and the solids were collected by filtration to provide the desired product as a white solid (TFA salt) (0.44 g, 78% yield). $^1$H NMR (300 MHz, CD$_3$OD) δ 3.72 (2H, td, J=13.3, 3.2 Hz), 3.55 (2H, q, J=7.2 Hz), 3.47 (2H, dd, J=12.6, 4.6 Hz), 3.35 (2H, q, J=7.2 Hz), 2.24 (2H, td, J=14.0, 5.0 Hz), 2.03 (2H, d, J=12.8 Hz), 1.26 (3H, t, J=7.1 Hz), 1.20 (3H, t, J=7.1 Hz). HRMS (M+H) calcd. for $C_{11}H_{20}N_3O_2$: 226.15556; found: 226.1551. CHN theoretical for 1.05 TFA: C, 45.61; H, 5.86; N, 12.18; F, 17.35; found: C, 45.81; H, 5.72; N, 12.08; F, 17.37.

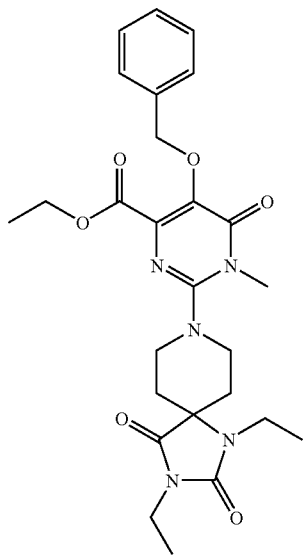

Intermediate 7E 2-(1,3-diethyl-2,4-dioxo-1,3,8-triazaspiro[4.5]dec-8-yl)-1,6-dihydro-1-methyl-6-oxo-5-(phenylmethoxy)-4-pyrimidinecarboxylic acid, ethyl ester The desired product was prepared following the procedure for Intermediate 5A from Intermediate 7D (0.44 g, 1.3 mmol), triethylamine (0.18 mL, 1.3 mmol), and Intermediate 1B (0.10 g, 0.27 mmol), stirring at 50° C. for 4 hours, diluting the mixture with water and ethyl acetate, washing the organic phase with 1N HCl, and concentrating to provide the desired product as a yellow oil (0.084 g, 61% yield). $^1$H NMR (300 MHz, CDCl$_3$) δ 7.45–7.40 (2H, m), 7.36–7.28 (3H, m), 5.13 (2H, s), 4.28 (2H, q, J=7.2 Hz), 3.75 (2H, td, J=13.5, 2.1 Hz), 3.53 (4H, t, J=7.3 Hz), 3.50 (3H, s), 3.27 (2H, q, J=7.2 Hz), 2.13 (2H, td, J=13.1, 4.5 Hz), 1.67 (2H, d, J=13.9 Hz), 1.28–1.15 (9H, m). LCMS (M+H) calcd. for $C_{26}H_{34}N_5O_6$: 512.25; found 512.24.

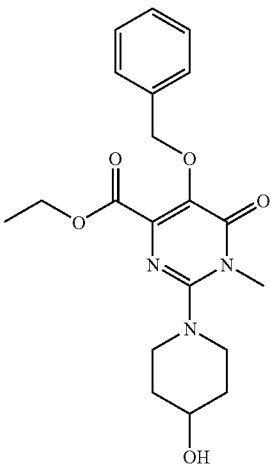

Intermediate 8A 1,6-dihydro-2-(4-hydroxypiperidin-1-yl)-1-methyl-5-(phenylmethoxy)-6-oxo-4-pyrimidinecarboxylic acid ethyl ester A suspension of 4-hydroxypiperidine (2.40 g, 23.8 mmol) and Intermediate 1B (1.83 g, 5.0 mmol) in THF (10 mL) was stirred at 40° C. for 18 hours. The solution was cooled to room temperature, washed with 1N HCl and brine, dried (Na$_2$SO$_4$), filtered, and concentrated to provide the desired product as a colorless oil (1.46 g, 76% yield). $^1$H NMR (300 MHz, CDCl$_3$) δ 7.44 (2H, dd, J=7.9, 1.6 Hz), 7.35–7.26 (3H, m), 5.12 (2H, s), 4.27 (2H, q, J=7.2 Hz), 3.91–3.82 (1H, m), 3.47 (3H, s), 3.43–3.35 (2H, m), 2.99–2.91 (2H, m), 2.01–1.93 (2H, m), 1.70–1.59 (2H, m), 1.26 (3H, t, J=7.1 Hz). LCMS (M+H) calcd. for C$_{20}$H$_{26}$N$_3$O$_5$: 388.18; found 388.38.

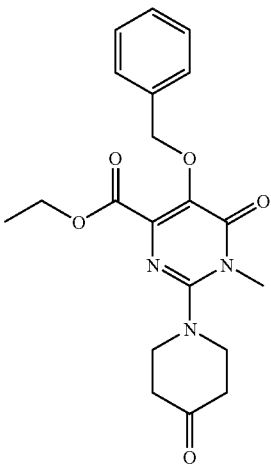

Intermediate 8B 1,6-dihydro-1-methyl-6-oxo-5-(phenylmethoxy)-2-(4-oxopiperidin-1-yl)-4-pyrimidinecarboxylic acid, ethyl ester A mixture of Intermediate 8A (1.30 g, 3.36 mmol), 4 Å molecular sieves, and 4-methylmorpholine N-oxide (0.58 g, 5.04 mmol) in CH$_2$Cl$_2$ (48 mL) was treated with tetrapropylammonium perruthenate (0.018 g, 0.05 mmol), stirred at room temperature for 18 hours, concentrated, and purified by flash chromatography eluting with 50–75% ethyl acetate/hexane to provide the desired product as a colorless oil that solidified to a white solid upon standing (1.085 g, 84% yield). $^1$H NMR (300 MHz, CDCl$_3$) δ 7.44 (2H, dd, J=7.9–1.6 Hz), 7.36–7.28 (3H, m), 5.15 (2H, s), 4.28 (2H, q, J=7.1 Hz), 3.55 (3H, s), 3.50 (4H, t, J=6.0 Hz), 2.58 (4H, t, J=6.0 Hz), 1.26 (3H, t, J=7.1 Hz). LCMS (M+H) calcd. for C$_{20}$H$_{24}$N$_3$O$_5$: 386.17; found 386.36.

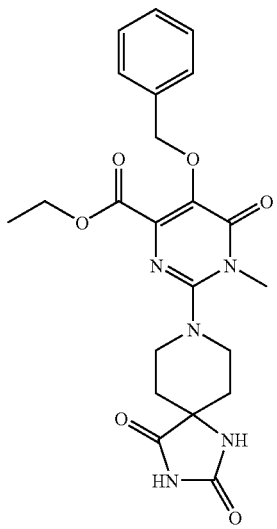

Intermediate 8C 1,6-dihydro-2-(2,4-dioxo-1,3,8-triazaspiro[4.5]dec-8-yl)-1-methyl-6-oxo-5-(phenylmethoxy)-4-pyrimidinecarboxylic acid, ethyl ester A solution of Intermediate 8B (0.50 g, 1.3 mmol) in ethanol (6.5 mL) was treated with a solution of ammonium carbonate (0.24 g, 2.6 mmol) in water (2.5 mL). Potassium cyanide (0.16 g, 2.6 mmol) was added and the mixture was stirred at 70° C. for 7 hours, then cooled to room temperature. The solids were collected by filtration and washed sequentially with water, minimal ethanol, and minimal diethyl ether to provide the desired product as a white solid (0.303 g, 51% yield). $^1$H NMR (500 MHz, CD$_3$OD) δ 7.45 (2H, d, J=7.0 Hz), 7.39–7.33 (3H, m), 5.12 (2H, s), 4.29 (2H, q, J=7.1 Hz), 3.62–3.55 (2H, m), 3.57 (3H, s), 3.22–3.17 (2H, m), 2.22–2.16 (2H, m), 1.83 (2H, d, J=13.7 Hz), 1.28 (3H, t, J=7.2 Hz). HRMS (M+H) calcd. for C$_{22}$H$_{26}$N$_5$O$_6$: 456.18832; found: 456.1895.

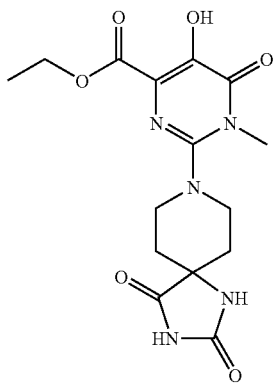

Intermediate 8D 1,6-dihydro-2-(2,4-dioxo-1,3,8-triazaspiro[4.5]dec-8-yl)-5-hydroxy-1-methyl-6-oxo-4-pyrimidinecarboxylic acid, ethyl ester A solution of Intermediate 8C (0.10 g, 0.22 mmol) in TFA (4 mL) was stirred at room temperature for 18 hours. The mixture was concentrated to give the product as a pale yellow oil that was used without further purification. LCMS (M+H) calcd. for $C_{15}H_{20}N_5O_6$: 366.14; found 366.19.

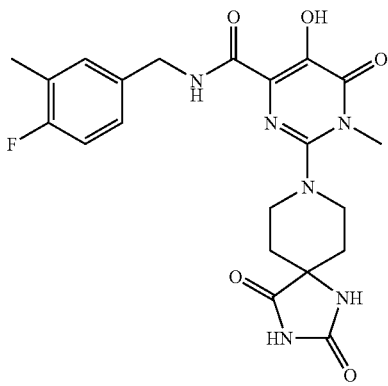

EXAMPLE 8

N-[4-fluoro-3-methylphenyl)methyl]-1,6-dihydro-2-(2,4-dioxo-1,3,8-triazaspiro[4.5]dec-8-yl)-5-hydroxy-1-methyl-6-oxo-4-pyrimidinecarboxamide The desired product was prepared following the procedure of Example 3 from Intermediate 8D (approximately 0.22 mmol) and (3-methyl-4-fluorobenzylamine (0.15 mL, 1.1 mmol) to provide the desired product as a white solid (0.040 g, 40% yield). $^1$H NMR (300 MHz, CD$_3$OD) δ 8.71 (1H, t, J=6.0 Hz), 7.25–7.17 (2H, m), 6.99 (1H, t, J=9.1 Hz), 4.53 (2H, s), 3.57 (3H, s), 3.54–3.48 (2H, m), 3.17–3.08 (2H, m), 2.27 (3H, d, J=1.8 Hz), 2.24–2.14 (2H, m), 1.81 (2H, d, J=14.6 Hz). HRMS (M+H) calcd. for $C_{21}H_{24}N_6O_5F$: 459.17923; found: 459.1804.

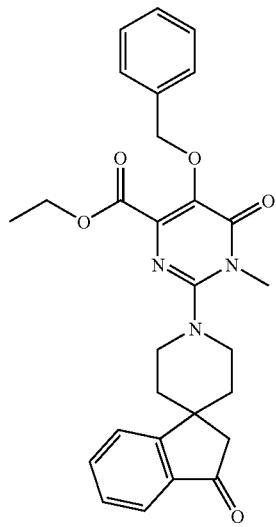

Intermediate 9A 2-(3,4-benzo-2-oxo-8-azaspiro[4.5]decan-2-yl)-1,6-dihydro-1-methyl-6-oxo-5-(phenylmethoxy)-4-pyrimidinecarboxylic acid, ethyl ester A suspension of 3,4-benzo-8-azaspiro[4.5]decan-2-one TFA (1.012 g, 3.2 mmol) in THF (3 mL) was treated with triethylamine (0.45 mL, 3.2 mmol) and stirred for 1 hour. Intermediate 1B (0.309 g, 0.84 mmol) was added and the resulting suspension was stirred at 70° C. for 2 hours, concentrated, and purified by flash chromatography eluting with 1:1 ethyl acetate/hexane to provide the desired product as a yellow foam (0.335 g, 82% yield). $^1$H NMR (300 MHz, CDCl$_3$) δ 7.73 (1H, d, J=7.7 Hz 7.67–7.62 (1H, m), 7.55 (1H, d, J=7.7 Hz), 7.47–7.28 (6H, m), 5.15 (2H, s), 4.30 (2H, q, J=7.2 Hz), 3.56 (3H, s), 3.52 (2H, d, J=15.4 Hz), 3.01 (2H, td, J=12.9, 1.7 Hz), 2.63 (2H, s), 2.18 (2H, td, J=13.2, 3.5 Hz), 1.63 (2H, d, J=13.2 Hz), 1.28 (3H, t, J=7.1 Hz). LCMS (M+H) calcd. for $C_{28}H_{29}N_3O_5$: 488.21; found: 488.22.

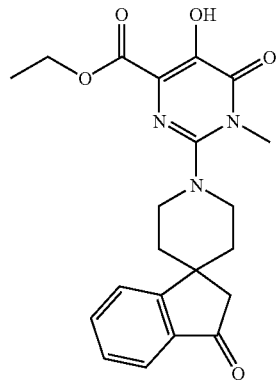

Intermediate 9B 2-(3,4-benzo-2-oxo-8-azaspiro[4.5]decan-2-yl)-1,6-dihydro-5-hydroxy-1-methyl-6-oxo-4-pyrimidinecarboxylic acid, ethyl ester A mixture of Intermediate 9A (0.335 g, 0.69 mmol) in TFA (10 mL) was stirred at room temp for 24 hours, concentrated, and triturated with diethyl ether to provide the desired product as a white solid. $^1$H NMR (300 MHz, CDCl$_3$) δ: 10.26 (1H, s), 7.74 (1H, d, J=7.7 Hz), 7.65 (1H, t, J=71. Hz), 7.55 (1H, d, J=7.7 Hz), 7.41 (1H, t, J=7.1 Hz), 4.42 (2H, q, J=7.1 Hz), 3.59 (3H, s), 3.42 (2H, d, J=10.6 Hz), 2.98 (2H, t, J=12.4 Hz), 2.65 (2H, s), 2.21 (2H, td, J=12.8

Hz), 1.64 (2H, d, J=13.2 Hz), 1.41 (3H, t, J=6.9 Hz). LCMS (M+H) calcd. for $C_{21}H_{24}N_3O_5$: 398.17; found: 398.23.

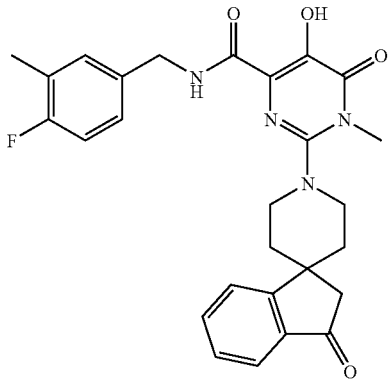

EXAMPLE 9

N-[(4-fluoro-3-methylphenyl)methyl]-2-(3,4-benzo-2-oxo-8-azaspiro[4.5]decan-2-yl)-1,6-dihydro-5-hydroxy-1-methyl-6-oxo-4-pyrimidinecarboxamide The desired product was prepared following the procedure of Example 3 from Intermediate 9B (0.069 g, 0.17 mmol) and (3-methyl-4-fluorobenzylamine (0.20 mL, 1.5 mmol) to provide the desired product as a white solid (0.013 g, 16% yield) and Example 10 as a white solid (0.066 g, 64% yield). $^1$H NMR (300 MHz, CDCl$_3$) δ 11.73 (1H, s), 7.75–7.72 (2H, m), 7.65 (1H, td, J=7.4, 1.2 Hz), 7.53 (1H, d, J=8.0 Hz), 7.42 (1H, t, J=7.3 Hz), 7.15–7.07 (2H, m), 6.96 (1H, t, J=8.8 Hz), 4.52 (2H, d, J=6.2 Hz), 3.58 (3H, s), 3.36 (2H, d, J=12.1 Hz), 2.93–2.84 (2H, m), 2.62 (2H, s), 2.24 (3H, s), 2.22–2.13 (2H, m), 1.63 (2H, d, J=13.5 Hz). HRMS (M+H) calcd. for $C_{27}H_{28}N_4O_4F$: 491.20947; found: 491.2095.

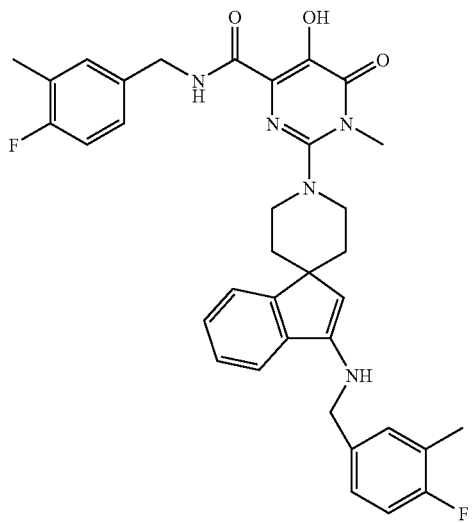

EXAMPLE 10

N-[(4-fluoro-3-methylphenyl)methyl]-2-[3-[[(4-fluoro-3-methylphenyl)methyl]amino]spiro[1H-indene-1,4'-piperidin]-1'-yl]-1,6-dihydro-5-hydroxy-1-methyl-6-oxo-4-pyrimidinecarboxamide HRMS (M+H) calcd for $C_{35}H_{36}N_5O_3F_2$: 612.27863; found: 612.2805.

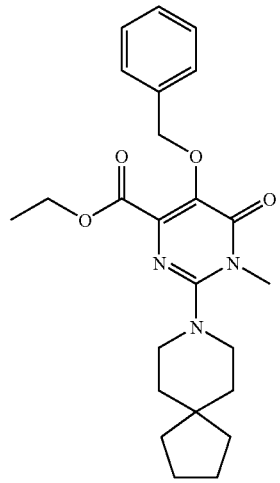

Intermediate 11A 2-(8-azaspiro[4.5]dec-8-yl)-1,6-dihydro-1-methyl-6-oxo-5-(phenylmethoxy)-4-pyrimidinecarboxylic acid ethyl ester A solution of Intermediate 1B (0.13 g, 0.36 mmol) in THF (1 mL) was treated with a suspension of 8-azaspiro[4.5]decane (0.25 g, 1.8 mmol) in triethylamine (0.20 mL, 1.5 mmol). The resulting mixture was stirred at 80° C. for 4 hours. The mixture was cooled to room temperature and the solids were removed by filtration. The organic solution was concentrated and the resulting residue was purified by flash chromatography eluting with 20% ethyl acetate/hexane to provide the desired product as a colorless oil (0.089 g, 58% yield). $^1$H NMR (300 MHz, CDCl$_3$) δ 7.45 ((2H, dd, J=7.9, 1.6 Hz), 7.35–7.27 (3H, m), 5.12 (3H, s), 4.29 (4H, q, J=7.2 Hz), 3.47 (3H, s), 3.11–3.07 (4H, m), 1.63–1.53 (8H, m), 1.46–1.42 (4H, m), 1.26 (3H, t, J=7.1 Hz). LCMS (M+H) calcd. for $C_{24}H_{32}N_3O_4$: 426.23; found: 426.22.

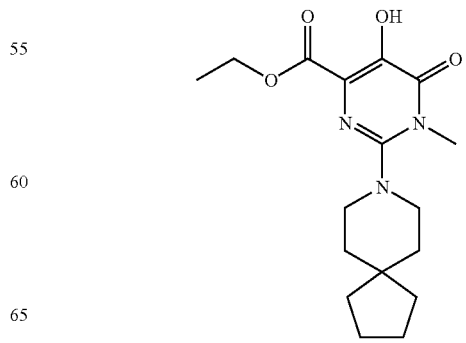

Intermediate 11B

2-(8-azaspiro[4,5]dec-8-yl)-1,6-dihydro-5-hydroxy-1-methyl-6-oxo-4-pyrimidinecarboxylic acid ethyl ester A mixture of Intermediate 11A (0.089 g, 0.21 mmol) in TFA (4 mL) was stirred at room tempure for 18 hours and concentrated to provide the desired product as a brown oil that was used without further purification. $^1$H NMR (300 MHz, CDCl$_3$) δ: 10.21 (1H, br s), 4.43 (2H, q, J=7.1 Hz), 3.55 (3H, s), 3.17–3.14 (4H, m), 1.65–1.58 (8H, m), 1.49–1.44 (4H, m), 1.39 (3H, t, J=7.0 Hz). LCMS (M+H) calcd. for C$_{17}$H$_{26}$N$_3$O$_4$: 336.19; found: 336.23.

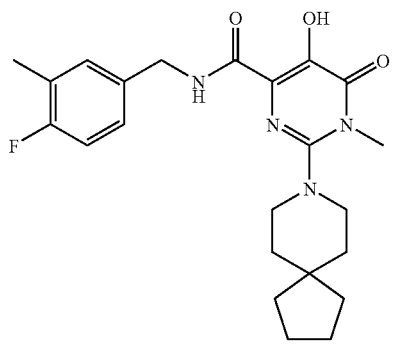

EXAMPLE 11

N-[(4-fluoro-3-methylphenyl)methyl]-2-(8-azaspiro[4.5]dec-8-yl)-1,6-dihydro-5-hydroxy-1-methyl-6-oxo-4-pyrimidinecarboxamide The desired product was prepared following the procedure for Example 3 from Intermediate 11B (0.21 mmol) and (3-methyl-4-fluorobenzylamine (0.14 mL, 1.1 mmol) to provide the desired product as a white solid (0.057 g, 64% yield). $^1$H NMR (300 MHz, CDCl$_3$) δ 11.61 (1H, s), 7.80 (1H, t, J=7.3 Hz), 7.15 (1H, d, J=7.3 Hz), 7.13–7.10 (1H, m), 6.98 (1H, t, J=8.8 Hz), 4.54 (2H, d, J=6.4 Hz 3.55 (3H, s), 2.98–2.96 (4H, m), 2.27 (3H, d, J=1.8 Hz), 1.65–1.62 (4H, m), 1.58–1.56 (4H, m), 1.48–1.45 (4H, m). HRMS (M+H) calcd. for C$_{23}$H$_{30}$N$_4$O$_3$F: 429.2302; found: 429.2315. CHN theoretical: C, 64.46; H, 6.82; N, 13.07; F, 4.43; found: C, 64.42; H, 6.94; N, 13.08; F, 4.77.

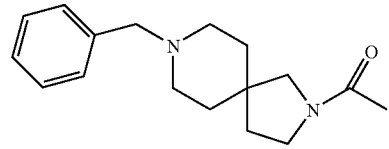

Intermediate 12A

1-benzyl-4-spiro-(1-pyrrolidin-3-yl)ethanon)piperidine

To a solution of 1-benzyl-4-spiro-(3-pyrrolidino)piperidine (0.5 g, 2.2 mmol) dissolved in pyridine (5 mL) was added acetyl chloride (0.17 mL, 2.4 mmol). The mixture was stirred at room temperature for 2 hours then concentrated. The residue was partitioned between ethyl acetate and water. The organic phase was washed with water, then brine, dried (Na$_2$SO$_4$), filtered, and concentrated to provide the desired product as a brown oil (0.168 g, 28% yield). $^1$H NMR (300 MHz, CDCl$_3$) δ 7.30–7.19 (5H, m), 3.51–3.42 (4H, m), 3.29–3.16 (2H, m), 2.59–2.21 (4H, m), 2.00 (3H, s), 180–1.67 (2H, m), 1.58–1.52 (4H, m). LCMS (M+H) calcd for C$_{17}$H$_{25}$N$_2$O: 273.19; found: 273.31.

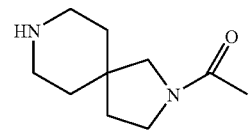

4-spiro-(1-(pyrrolidin-3-yl)ethanone)piperidine hydrochloride

Intermediate 12A (0.168 g, 0.62 mmol) was dissolved in ethanol (10 mL). To this solution was added 1N HCl (2 mL) and 10% Pd/C (100 mg). The mixture was shaken under H$_2$ at 40 psi for 18 hours, filtered through diatomaceous earth (Celite®), and concentrated to provide the desired product as a yellow oil (0.159 g). $^1$H NMR (300 MHz, CDCl$_3$) δ 3.66 (2H, dt, J=31.0, 7.11 Hz), 3.51 (2H, d, J=35.9 Hz), 3.27–3.20 (4H, m), 2.18 (3H, d, J=11.0 Hz), 2.00 (2H, dt, J=21.6, 7.1 Hz), 187–183 (4H, m).

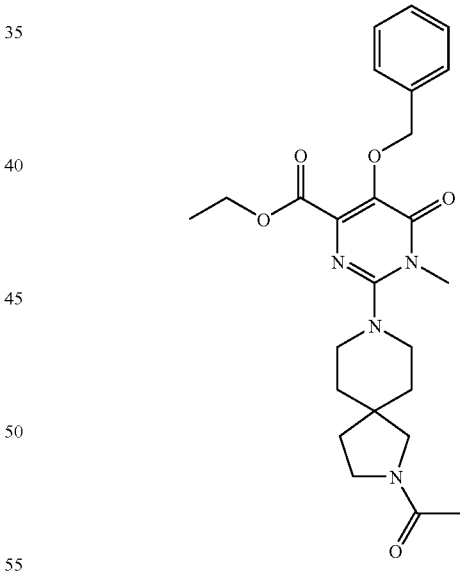

Intermediate 12C

2-(2-(1-ethanone)-2,8-diazaspiro[4.5]dec-8-yl)-1,6-dihydro-1-methyl-6-oxo-5-(phenylmethoxy)-4-pyrimidinecarboxylic acid ethyl ester To a stirred mixture of Intermediate 12B (0.15 g, 0.69 mmol) and triethylamine (0.096 mL, 0.69 mmol) in THF (2 mL) was added Intermediate 1B (0.18 g, 0.49 mmol). The resulting mixture was stirred at 90° C. for 18 hours, cooled, concentrated, and purified by chromatography (YMC Combiprep ODS-A, 30 mm×50 mm, methanol/H₂O/0.1% TFA) to provide the desired product as a colorless oil (0.025 g, 11% yield). LCMS [M+H]⁺ calcd for $C_{25}H_{33}N_4O_5$: 469.24; found: 469.29.

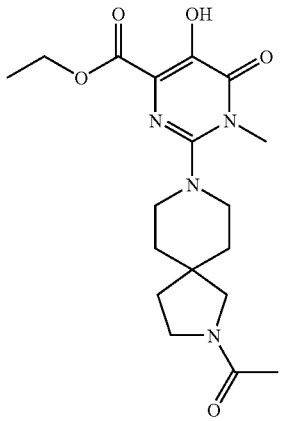

Intermediate 12D 2-(2-(1-ethanone)-2,8-diazaspiro[4.5]dec-8-yl)-1,6-dihydro-5-hydroxy-1-methyl-6-oxo-4-pyrimidinecarboxylic acid ethyl ester A solution of Example 12C (0.025 g, 0.05 mmol) in TFA (3 mL) was stirred at room temp for 4 hours and concentrated to provide the desired product as a brown oil that was used without purification. LCMS [M+H]⁺ calcd for $C_{18}H_{27}N_4O_5$: 379.19; found: 379.34.

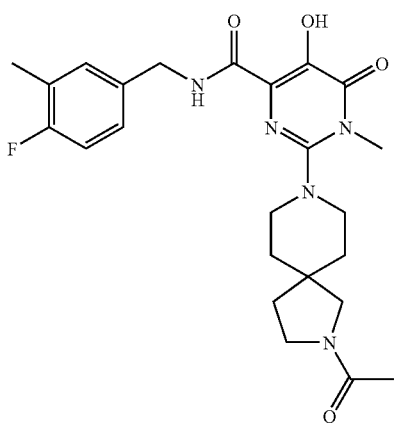

EXAMPLE 12

N-(4-fluoro-3-methylbenzyl)-5-hydroxy-1-methyl-6-oxo-2-(1-ethanone)-2,8-diazaspiro[4.5]dec-8-yl)-1,6-dihydropyrimidine-4-carboxamide A mixture of Intermediate 12D (0.019 g, 0.05 mmol), 3-methyl-4-fluorobenzylamine (0.03 mL, 0.22 mmol) and triethylamine (0.05 mL) in DMF (0.5 mL) was heated at 80° C. for 2 hours. Then cooled and purified by chromatography (YMC Combiprep ODS-A, 30 mm×50 mm, methanol/H₂O/0.1% TFA) to provide the desired product as a colorless oil (0.0048 g, 20% yield over two steps). ¹H NMR (300 MHz, CD₃OD) δ 7.25–7.17 (2H, m), 6.99 (1H, t, J=9.0 Hz), 4.52 (2H, s), 3.67–3.48 (2H, m), 3.56 (3H, s), 3.36 (2H, s), 3.23–2.97 (4H, m), 2.26 (3H, s), 2.07 (3H, s), 2.08–1.73 (6H, m). HRMS (M+H) calcd for $C_{24}H_{31}N_5O_4F$: 472.23602; found: 472.2363.

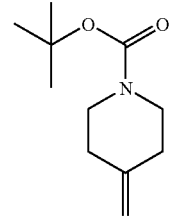

Intermediate 13A tert-butyl 4-methylenepiperidine-1-carboxylate

Methyltriphenylphosphonium bromide (9.5 g, 26.7 mmol) was dissolved in THF (33 mL). Sodium hydride (0.675 g, 26.7 mmol) was added portionwise followed by DMSO (33 mL). After stirring for 10 minutes, a solution of tert-butyl 4-oxopiperidine-1-carboxylate (5.0 g, 25 mmol) in THF (25 mL) was added dropwise. The resulting suspension was stirred at room temp for 30 minutes. Water and ethyl acetate were added and the organic phase was washed with aqueous NaHCO₃ and brine and was dried (Na₂SO₄), filtered, and concentrated. The colorless oil was triturated with diethyl ether and the resulting solids were removed by filtration. Concentration of the solvent gave an oil that was purified by flash chromatography eluting with 30%–50% diethyl ether/hexane to provide the desired product as a colorless oil (2.69 g, 55% yield). ¹H NMR (300 MHz, CDCl₃) δ: 4.70 (2H, s), 3.38 (4H, t, J=5.7 Hz), 2.14 (4H, t, J=5.8 Hz), 1.43 (9H, s).

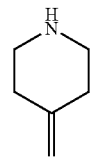

Intermediate 13B 4-methylenepiperidine trifluoroacetate

To a solution of Intermediate 13A (1.25 g, 6.3 mmol) dissolved in CH₂Cl₂ (2 mL) was added TFA (3 mL) and the solution stirred at room temperature for 24 hours. Concentration of the solution provided the desired product as a colorless oil (2.11 g). ¹H NMR (300 MHz, CDCl₃) δ 10.43 (1H, s), 4.92 (2H, s), 3.28–3.21 (4H, m), 2.51–2.47 (4H, m).

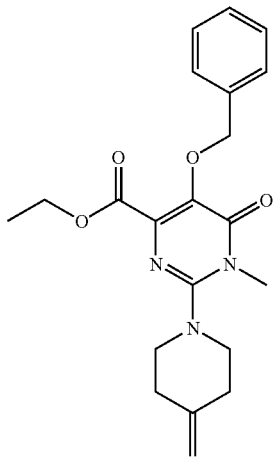

Intermediate 13C ethyl-5-(benzyloxy)-1-methyl-2-(4-methylenepiperidin-1-yl)-6-oxo-1,6-dihydropyrimidine-4-carboxylate A solution of Intermediate 1B (1.15 g, 3.15 mmol), Intermediate 13B (2.11 g, 6.3 mmol), and triethylamine (1.3 mL) in THF (2 mL) was stirred at 90° C. for 6 hours. The mixture was cooled, concentrated, and purified by flash chromatography (10%–30%–50% ethyl acetate/hexane) to provide the desired product as a white solid (0.39 g, 32% yield). $^1$H NMR (500 MHz, CDCl$_3$) δ 7.47 (2H, d, J=7.3 Hz), 7.36–7.29 (3H, m), 5.15 (2H, s), 4.79 (2H, s), 4.31 (2H, q, J=7.1 Hz), 3.54 (3H, s), 3.21–3.19 (4H, m), 2.37–2.35 (4H, m), 1.29 (3H, t, J=7.2 Hz). LCMS (M+H) calcd for C$_{21}$H$_{26}$N$_3$O$_4$: 384.19; found 384.27.

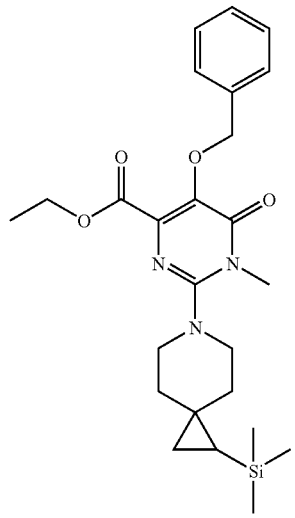

Intermediate 13D 2-(1-trimethylsilane-6-azaspiro[4.3]oct-6-yl)-1,6-dihydro-1-methyl-6-oxo-5-(phenylmethoxy)-4-pyrimidinecarboxylicacid ethyl ester To a solution of Intermediate 13C (0.39 g, 1.0 mmol) in benzene (4 mL) was added catalytic rhodium acetate dimer. Trimethylsilyl diazomethane (0.50 mL, 1.0 mmol, 2M in hexane) was added dropwise over 24 hours using a syringe pump. Additional rhodium acetate dimmer and trimethylsilyl diazomethane were added in the same fashion over two more days. The resulting mixture was stirred at room temperature for 18 hours, concentrated to half the original volume, and purified by flash chromatography (eluting with 0%–15% ethyl acetate/hexane) to provide the desired product as a yellow oil (0.35 g, 75% yield). $^1$H NMR (300 MHz, CDCl$_3$) δ 7.47–7.44 (2H, m), 7.35–7.27 (3H, m), 5.12 (2H, s), 4.29 (2H, q, J=7.1 Hz), 3.49 (3H, s), 3.29–3.24 (2H, m), 3.13–3.00 (2H, m), 1.84–1.77 (2H, m), 1.34–1.14 (2H, m), 1.26 (3H, t, J=7.1 Hz), 0.58 (1H, dd, J=10.2, 3.3 Hz), 0.32 (1H, dd, J=6.9, 3.6 Hz), 0.01 (9H, s), −0.44 (1H, dd, J=10.1, 7.5 Hz). LCMS (M+H) calcd for C$_{25}$H$_{36}$N$_3$O$_4$Si: 470.24; found 470.38.

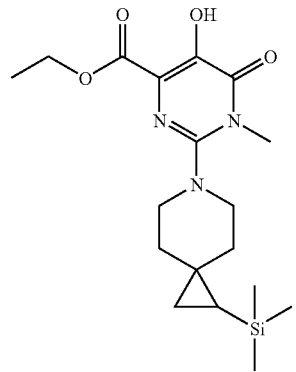

Intermediate 13E 2-(1-trimethylsilane-6-azaspiro[4.3]oct-6-yl)-1,6-dihydro-5-hydroxy-1-methyl-6-oxo-4-pyrimidinecarboxylic acid ethyl ester and

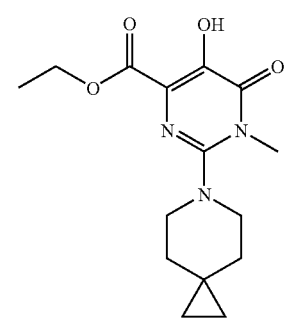

Intermediate 13F 2-(6-azaspiro[4.3]oct-6-yl)-1,6-dihydro-5-hydroxy-1-methyl-6-oxo-4-pyrimidinecarboxylic acid ethyl ester Intermediate 13D (0.29 g, 0.61 mmol) was stirred in TFA (4 mL) at room temperature for 6 hours. Concentration and purification by chromatography (YMC Combiprep ODS-A, 30 mm×50 mm, methanol/H$_2$O/0.1% TFA) gave intermediate 13E as a brown oil (0.027 g, 11% yield) and Intermediate 13F as a white solid (0.12 g, 65% yield).

Intermediate 13E: $^1$H NMR (500 MHz, CDCl$_3$) δ: 4.43 (2H, q, J=7.1 Hz), 3.64 (1H, br s), 3.53 (3H, d, J=2.7 Hz), 3.25 (1H, d, J=13.1 Hz), 3.19 (1H, t, J=5.6 Hz), 3.05 (1H, t, J=12.3 Hz), 2.40 (1H, d, J=14.0 Hz), 2.24 (1H, br s), 2.04–1.97 (2H, m), 1.87–1.81 (1H, m), 1.42 (3H, dt, J=7.2, 2.4 Hz), 0.66–0.62 (1H, m), 0.45–0.41 (1H, m), 0.01 (9H, s). LCMS (M+H) calcd for C$_{18}$H$_{30}$N$_3$O$_4$Si: 380.20; found 380.27.

Intermediate 13F: $^1$H NMR (300 MHz, CDCl$_3$) δ: 4.42 (2H, q, J=7.1 Hz), 3.54 (3H, s), 3.15 (4H, t, J=5.3 Hz), 1.51–1.48 (4H, m), 1.40 (3H, t, J=7.1 Hz), 0.35 (4H, s). HRMS (M+H) calcd for C$_{15}$H$_{22}$N$_3$O$_4$: 308.16104; found: 308.1614.

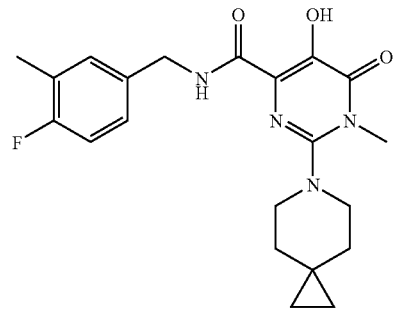

EXAMPLE 14

N-(4-fluoro-3-methylbenzyl)-5-hydroxy-1-methyl-6-oxo-2-(6-azaspiro[4.3]oct-6-yl)-1,6-dihydropyrimidine-4-carboxamide Following the procedure for Example 1, using Intermediate 13F (0.10 g, 0.32 mmol), triethylamine (0.10 mL, 0.72 mmol), and 4-fluoro-3-methylbenzylamine (0.084 mL, 0.64 mmol) the desired product was prepared as a white foam (0.084 g, 66% yield). $^1$H NMR (300 MHz, CDCl$_3$) δ 11.62 (1H, br s), 7.81 (1H, t, J=5.8 Hz), 7.14 (1H, d, J=7.3 Hz), 7.13–7.10 (1H, m), 6.98 (1H, t, J=8.8 Hz), 4.53 (2H, d, J=6.1 Hz), 3.55 (3H, s), 3.06 (4H, t, J=5.3 Hz), 2.27 (3H, d, J=1.8 Hz), 1.50 (4H, br s), 0.37 (4H, s). HRMS (M+H) calcd for C$_{21}$H$_{26}$N$_4$O$_3$F: 401.1981; found: 401.2008. Anal. Calcd for C$_{21}$H$_{25}$N$_4$O$_3$F.0.3H$_2$O.0.25 TFA: C, 59.45; H, 6.00; N, 12.90; F, 7.65; found: C, 59.19; H, 5.69; N, 12.82; F, 7.27.

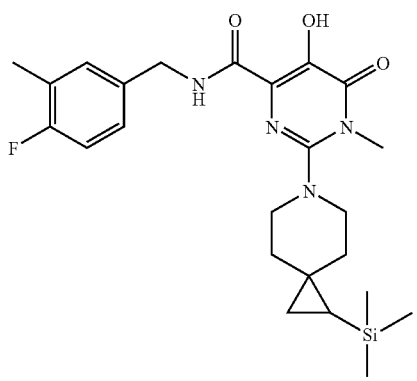

EXAMPLE 13

N-(4-fluoro-3-methylbenzyl)-5-hydroxy 1-methyl-6-oxo-2-(1-trimethylsilane-6-azaspiro[4.3]oct-6-yl)-1,6-dihydropyrimidine-4-carboxamide Following the procedure for Example 1, using Intermediate 13E (0.027 g, 0.07 mmol), triethylamine (0.02 mL, 0.16 mmol), and 4-fluoro-3-methylbenzylamine (0.018 mL, 0.14 mmol) the desired product was prepared as a brown oil (0.016 g, 49% yield). $^1$H NMR (300 MHz, CDCl$_3$) δ 11.5 (1H, br s), 7.77 (1H, t, J=5.6 Hz), 7.14 (1H, d, J=7.0 Hz), 7.12–7.09 (1H, m), 6.98 (1H, t, J=8.8 Hz), 4.53 (2H, d, J=6.4 Hz), 3.57 (2H, br s), 3.54 (3H, s), 3.14 (2H, t, J=5.6 Hz), 2.27 (3H, s), 2.22 (2H, br s), 2.01 (2H, t, J=8.2 Hz), 0.64–0.61 (3H, m), 0.01 (9H, s). HRMS (M+H) calcd for C$_{24}$H$_{34}$N$_4$O$_3$FSi: 473.23843; found: 473.2393.

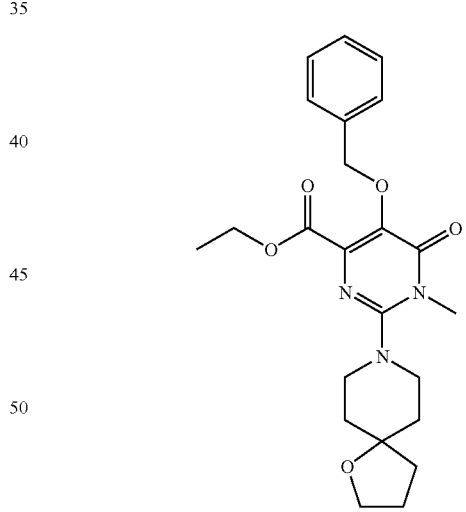

Intermediate 15A 1,6-dihydro-1-methyl-2-(1-oxa-8-azaspiro[4.5]dec-8-yl)-6-oxo-5-(phenylmethoxy)-4-pyrimidinecarboxylic acid ethyl ester A suspension of the 1-oxa-8-azaspiro[4.5]decane hydrochloride (0.264 g, 1.49 mmol; prepared according to the procedure by WO 0187838, 2001), triethylamine (0.21 mL, 1.5 mmol) and THF (3 mL) was stirred for 30 minutes at room temperature. The mixture was treated with Intermediate 1B (0.18 g, 0.50 mmol) and stirred at room temperature for 4 days and concentrated. The resulting residue was purified by flash chromatography eluting with 0%–20%–50% ethyl acetate/hexane to provide the desired product as a yellow oil (0.139 g, 65% yield). $^1$H NMR (300 MHz, CDCl$_3$) δ: 7.46–7.43 (1H, m), 7.35–7.27 (2H, m), 5.12 (2H, s), 4.28 (2H, q J=7.2 Hz), 3.82 (2H, t, J=6.8 Hz), 3.47 (3H, s), 3.31–3.23 (2H, m), 3.18–3.10 (2H, m), 1.97–1.87 (2H, m), 1.74–1.69 (4H, m), 1.55 (2H, br s), 1.26 (3H, t, J=7.1 Hz). LCMS (M+H) calcd for C$_{23}$H$_{30}$N$_3$O$_5$: 428.21; found: 428.32.

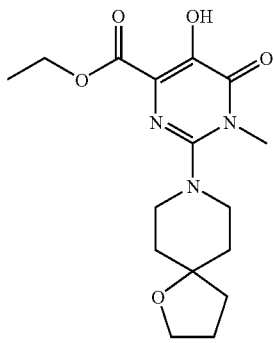

Intermediate 15B 1,6-dihydro-5-hydroxy-1-methyl-2-(1-oxa-8-aza-spiro[4.5]dec-8-yl)-6-oxo-4-pyrimidinecarboxylic acid ethyl ester A solution of Intermediate 15A (0.139 g, 0.32 mmol) in TFA (4 mL) was stirred at room temperature for 18 h and concentrated. The crude residue was used in next step without purification. $^1$H NMR (500 MHz, CDCl$_3$) δ 4.45 (2H, q, J=7.1 Hz), 3.96 (2H, t, J=6.7 Hz), 3.58 (3H, s), 3.38–3.33 (2H, m), 3.18–3.13 (2H, m), 2.06–2.01 (2H, m), 1.91–1.77 (6H, m), 1.41 (3H, t, J=7.2 Hz). LCMS (M+H) calcd for C$_{16}$H$_{24}$N$_3$O$_5$: 338.17; found: 338.20.

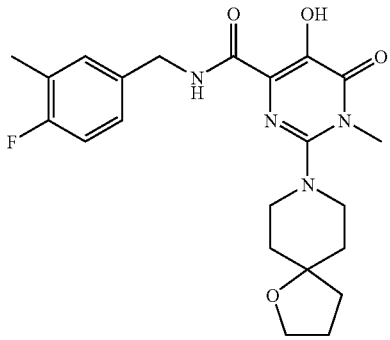

EXAMPLE 15

N-[(4-fluoro-3-methylphenyl)methyl]-1,6-dihydro-5-hydroxy-1-methyl-2-(1-oxa-8-azaspiro[4.5]dec-8-yl)-6-oxo-4-pyrimidinecarboxamide A solution of Intermediate 15B (0.32 mmol), triethylamine (0.053 mL, 0.38 mmol) and 3-methyl-4-fluorobenzylamine (0.21 mL, 1.6 mmol) in DMF (1 mL) was stirred at 90° C. for 1.5 hours. The mixture was cooled and purified by chromatography (YMC Combiprep ODS-A, 30 mm×50 mm, methanol/H$_2$O/0.1% TFA) to provide the desired product as a white foam (0.072 g, 53% yield). $^1$H NMR (300 MHz, CDCl$_3$) δ 11.60 (1H, s), 7.76 (1H, br s), 7.12–7.06 (2H, m), 6.95 (1H, t, J=8.8 Hz), 4.48 (2H, d, J=5.9 Hz), 3.87 (2H, t, J=6.8 Hz), 3.49 (3H, s), 3.12–2.97 (4H, m), 2.22 (3H, s), 1.97–1.88 (2H, m), 1.74–1.70 (6H, m). HRMS (M+H) calcd for C$_{22}$H$_{28}$N$_4$O$_4$F: 431.20947; found: 431.2105.

By substituting the appropriate reagents into the schemes and the above examples, the following compounds can be prepared:

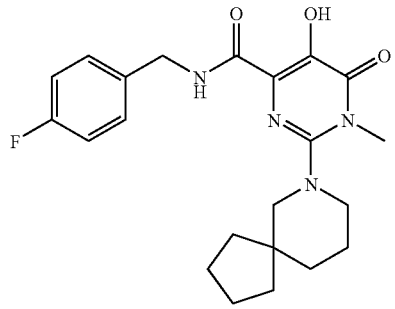

EXAMPLE 16

N-[(4-fluorophenyl)methyl]-1,6-dihydro-5-hydroxy-1-methyl-6-oxo-2-(7-azaspiro[4.5]dec-7-yl)-4-pyrimidinecarboxamide

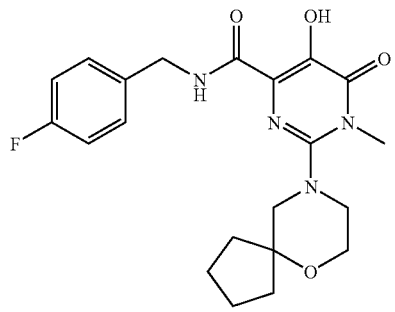

EXAMPLE 17

N-[(4-fluorophenyl)methyl]-1,6-dihydro-5-hydroxy-1-methyl-6-oxo-2-(6-oxa-9-azaspiro[4.5]dec-9-yl)-4-pyrimidinecarboxamide

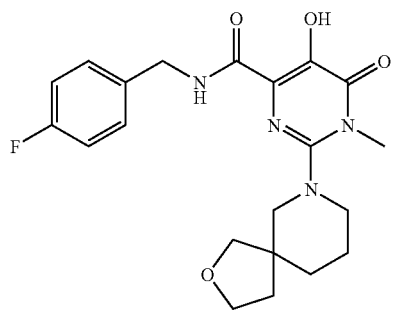

EXAMPLE 18

N-[(4-fluorophenyl)methyl]-1,6-dihydro-5-hydroxy-1-methyl-6-oxo-2-(2-oxa-7-azaspiro[4.5]dec-7-yl)-4-pyrimidinecarboxamide

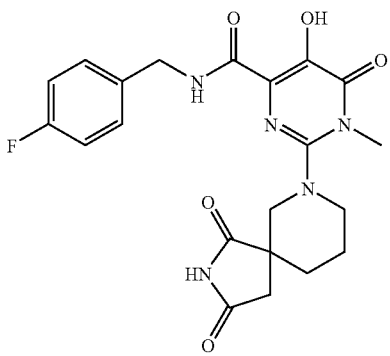

EXAMPLE 19

N-[(4-fluorophenyl)methyl]-1,6-dihydro-5-hydroxy-1-methyl-6-oxo-2-(1,3-dioxo-2,7-diazaspiro[4.5]dec-7-yl)-4-pyrimidinecarboxamide

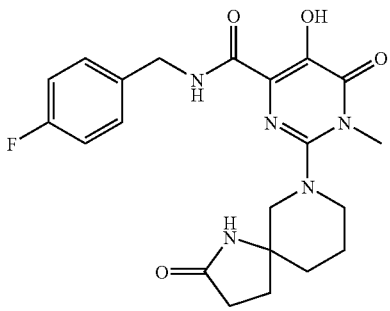

EXAMPLE 20

N-[(4-fluorophenyl)methyl]-1,6-dihydro-5-hydroxy-1-methyl-6-oxo-2-(2-oxo-1,7-diazaspiro[4.5]dec-7-yl)-4-pyrimidinecarboxamide

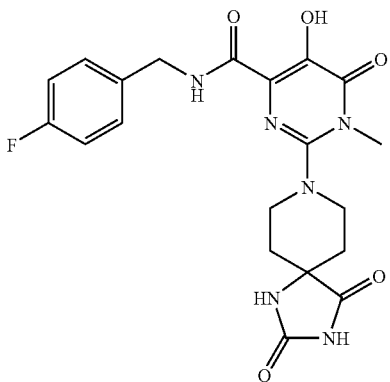

EXAMPLE 21

N-[(4-fluorophenyl)methyl]-1,6-dihydro-5-hydroxy-1-methyl-6-oxo-2-(2,4-dioxo-1,3,8-triazaspiro[4.5]dec-8-yl)-4-pyrimidinecarboxamide

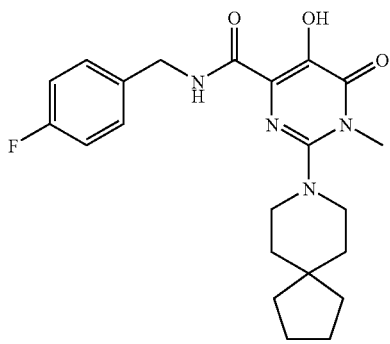

EXAMPLE 22

N-[(4-fluorophenyl)methyl]-1,6-dihydro-5-hydroxy-1-methyl-6-oxo-2-(8-azaspiro[4.5]dec-8-yl)-4-pyrimidinecarboxamide

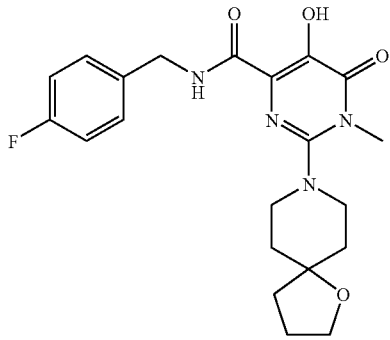

EXAMPLE 23

N-[(4-fluorophenyl)methyl]-1,6-dihydro-5-hydroxy-1-methyl-6-oxo-2-(1-oxa-8-azaspiro[4.5]dec-8-yl)-4-pyrimidinecarboxamide

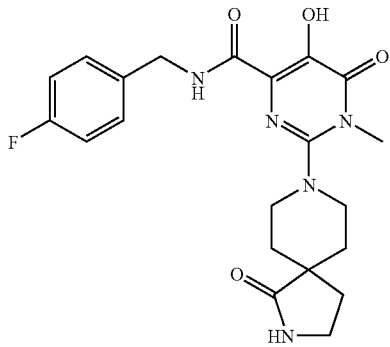

EXAMPLE 24

N-[(4-fluorophenyl)methyl]-1,6-dihydro-5-hydroxy-1-methyl-6-oxo-2-(1-oxo-2,8-diazaspiro[4.5]dec-8-yl)-4-pyrimidinecarboxamide

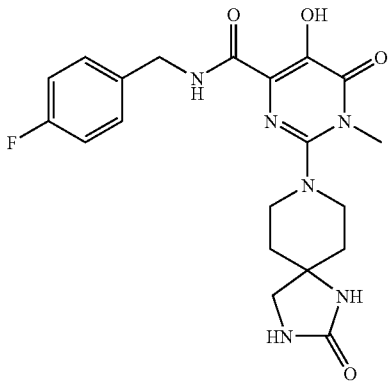

EXAMPLE 25

N-[(4-fluorophenyl)methyl]-1,6-dihydro-5-hydroxy-1-methyl-6-oxo-2-(2-oxo-1,3,8-triazaspiro[4.5]dec-8-yl)-4-pyrimidinecarboxamide

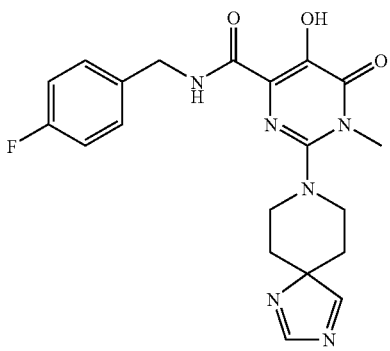

EXAMPLE 26

N-[(4-fluorophenyl)methyl]-1,6-dihydro-5-hydroxy-1-methyl-6-oxo-2-(1,3,8-triazaspiro[4.5]deca-1,3-dien-8-yl)-4-pyrimidinecarboxamide

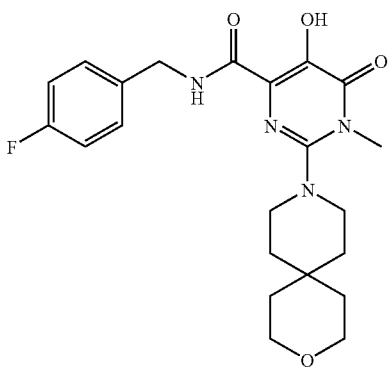

EXAMPLE 27

N-[(4-fluorophenyl)methyl]-1,6-dihydro-5-hydroxy-1-methyl-6-oxo-2-(3-oxa-9-azaspiro[5.5]undec-9-yl)-4-pyrimidinecarboxamide

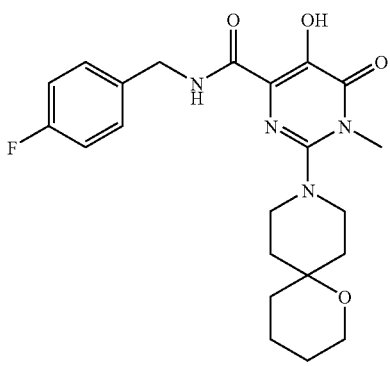

EXAMPLE 28

N-[(4-fluorophenyl)methyl]-1,6-dihydro-5-hydroxy-1-methyl-6-oxo-2-(1-oxa-9-azaspiro[5.5]undec-9-yl)-4-pyrimidinecarboxamide

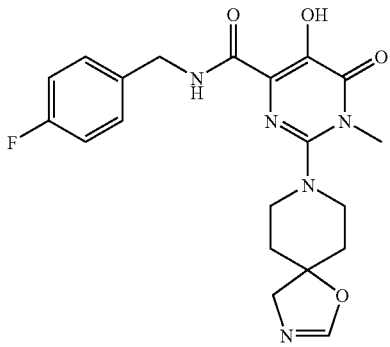

EXAMPLE 29

N-[(4-fluorophenyl)methyl]-1,6-dihydro-5-hydroxy-1-methyl-6-oxo-2-(1-oxa-3,8-diazaspiro[4.5]dec-2-en-8-yl)-4-pyrimidinecarboxamide

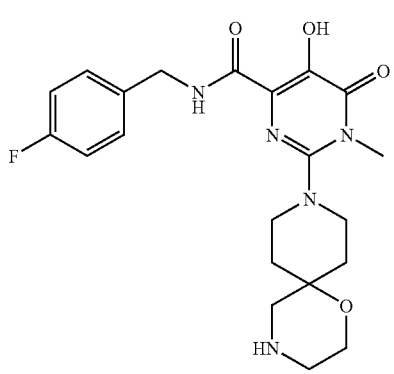

EXAMPLE 30

N-[(4-fluorophenyl)methyl]-1,6-dihydro-5-hydroxy-1-methyl-6-oxo-2-(1-oxa-4,9-diazaspiro[5.5]undec-9-yl)-4-pyrimidinecarboxamide

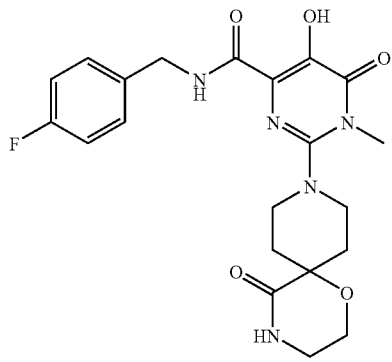

EXAMPLE 31

N-[(4-fluorophenyl)methyl]-1,6-dihydro-5-hydroxy-1-methyl-6-oxo-2-(5-oxo-1-oxa-4,9-diazaspiro[5.5]undec-9-yl)-4-pyrimidinecarboxamide

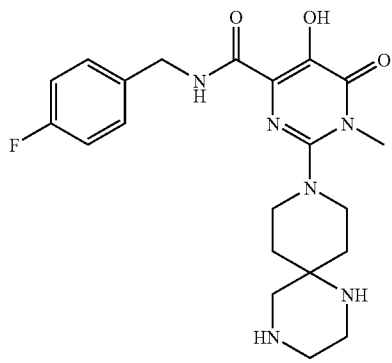

EXAMPLE 32

N-[(4-fluorophenyl)methyl]-1,6-dihydro-5-hydroxy-1-methyl-6-oxo-2-(1,4,9-triazaspiro[5.5]undec-9-yl)-4-pyrimidinecarboxamide

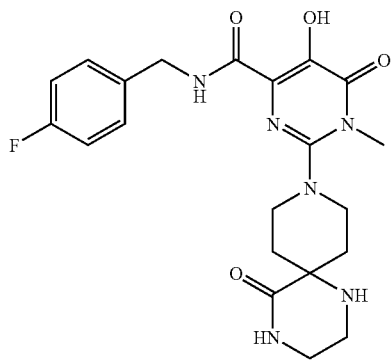

EXAMPLE 33

N-[(4-fluorophenyl)methyl]-1,6-dihydro-5-hydroxy-1-methyl-6-oxo-2-(5-oxo-1,4,9-triazaspiro[5.5]undec-9-yl)-4-pyrimidinecarboxamide Determination of Biological Activity To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908–5911 (1995). The sequences of substrate and target DNA were described in *Nucleic Acid Research* 22,1121–1122 (1994). Using this assay Examples 1–15 were found to have $IC_{50}$'s of between about 0.01 and about 0.2 μM.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

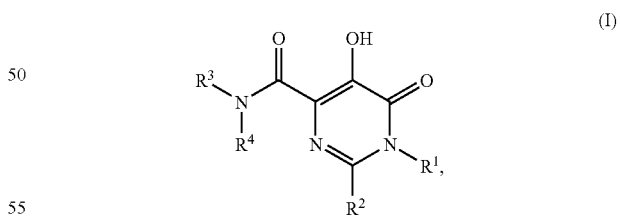

or a pharmaceutically acceptable salt thereof, wherein $R^1$ is selected from hydrogen, alkenyl, alkoxyalkyl, alkyl, and arylalkyl;

$R^2$ is a 3- to 8-membered saturated or partially unsaturated ring containing one to three heteroatoms selected from N, O, and $S(O)_n$, wherein n is 0, 1, or 2; wherein said ring is attached through a nitrogen atom, and wherein said ring is substituted by a 3- to 10-membered monocyclic or bicyclic spirocycle containing from zero to three heteroatoms selected from N, O, and S(O)$_n$, wherein n is 0, 1, or 2; and wherein said ring and said spirocycle are each optionally substituted with one to three substituents independently selected from alkoxy, alkyl, alkylcarbonyl, aryl, halo, heteroaryl, heterocyclyl, —NR$^a$R$^b$, oxo, thiooxo, and trialkylsilyl;

R$^3$ and R$^4$ are independently selected from hydrogen, aryl, arylalkyl, heteroaryl, heteroarylalkyl, heterocyclyl, and heterocyclylalkyl; and R$^a$ and R$^b$ are independently selected from hydrogen, alkyl, aryl, and arylalkyl.

2. The compound of claim 1 wherein R$^1$ is alkyl.

3. The compound of claim 1 wherein R$^3$ and R$^4$ are independently selected from the group consisting of hydrogen and arylalkyl.

4. A compound of formula (II),

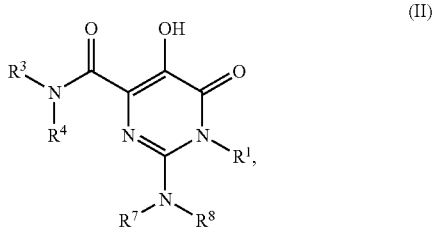

(II)

or a pharmaceutically acceptable salt thereof, wherein

R$^1$ is selected from hydrogen, alkenyl, alkoxyalkyl, alkyl, and arylalkyl;

R$^3$ and R$^4$ are independently selected from hydrogen, aryl, arylalkyl, heteroaryl, heteroarylalkyl, heterocyclyl, and heterocyclylalkyl;

R$^7$ and R$^8$, together with the nitrogen atom to which they are attached, form a 3- to 8-membered saturated or partially unsaturated ring containing zero to two additional heteroatoms selected from N, O, and S(O)$_n$, wherein n is 0, 1, or 2; wherein said ring is substituted by a 3- to 10-membered monocyclic or bicyclic spirocycle containing from zero to three heteroatoms selected from N, O, and S(O)$_n$, wherein n is 0, 1, or 2; and wherein said ring and said spirocycle are each optionally substituted with one to three substituents independently selected from alkoxy, alkyl, alkylcarbonyl, aryl, halo, heteroaryl, heterocyclyl, —NR$^a$R$^b$, oxo, thiooxo, and trialkylsilyl; and R$^a$ and R$^b$ are independently selected from hydrogen, alkyl, aryl, and arylalkyl.

5. The compound of claim 4 wherein R$^1$ is alkyl.

6. The compound of claim 4 wherein R$^3$ and R$^4$ are independently selected from the group consisting of hydrogen and arylalkyl.

7. The compound of claim 4 wherein
R$^1$ is alkyl;
R$^3$ and R$^4$ are independently selected from hydrogen, and arylalkyl; and
R$^7$ and R$^8$, together with the nitrogen atom to which they are attached, form piperidinyl ring substituted by a 5- to 9-membered monocyclic or bicyclic spirocycle containing from zero to three heteroatoms selected from N, O, and S(O)$_n$, wherein n is 0, 1, or 2; and wherein said piperidinyl and said spirocycle are each optionally substituted with one to three substituents independently selected from alkoxy, alkyl, alkylcarbonyl, aryl, halo, heteroaryl, heterocyclyl, —NR$^a$R$^b$, oxo, thiooxo, and trialkylsilyl.

8. A compound selected from
2-(1,4-dioxa-8-azaspiro[4.5]dec-8-yl)-N-[(4-fluorophenyl)methyl]-1,6-dihydro-5-hydroxy-1-methyl-6-oxo-4-pyrimidinecarboxamide;
2-(1,4-dioxa-8-azaspiro[4.5]dec-8-yl)-N-[(4-fluoro-3-methylphenyl)methyl]-1,6-dihydro-5-hydroxy-1-methyl-6-oxo-4-pyrimidinecarboxamide;
N-[(4-fluorophenyl)methyl]-1,6-dihydro-5-hydroxy-1-methyl-6-oxo-2-(4-oxo-1-phenyl-1,3,8-triazaspiro[4.5]dec-8-yl)-4-pyrimidinecarboxamide;
N-[(4-fluoro-3-methylphenyl)methyl]-1,6-dihydro-5-hydroxy-1-methyl-6-oxo-2-(4-oxo-1-phenyl-1,3,8-triazaspiro[4.5]dec-8-yl)-4-pyrimidinecarboxamide;
N-[(4-fluoro-3-methylphenyl)methyl]-1,6-dihydro-5-hydroxy-1-methyl-2-(2-methyl-1-oxo-2,8-diazaspiro[4.5]dec-8-yl)-6-oxo-4-pyrimidinecarboxamide;
N-[(4-fluoro-3-methylphenyl)methyl]-1,6-dihydro-5-hydroxy-1-methyl-2-(3-oxa-8-azaspiro[5.5]undec-8-yl)-6-oxo-4-pyrimidinecarboxamide;
N-[4-fluoro-3-methylphenyl)methyl]-2-(1,3-diethyl-2,4-dioxo-1,3,8-triazaspiro[4.5]dec-8-yl)-1,6-dihydro-5-hydroxy-1-methyl-6-oxo-4-pyrimidinecarboxamide;
N-[4-fluoro-3-methylphenyl)methyl]-1,6-dihydro-2-(2,4-dioxo-1,3,8-triazaspiro[4.5]dec-8-yl)-5-hydroxy-1-methyl-6-oxo-4-pyrimidinecarboxamide;
N-[(4-fluoro-3-methylphenyl)methyl]-2-(3,4-benzo-2-oxo-8-azaspiro[4.5]decan-2-yl)-1,6-dihydro-5-hydroxy-1-methyl-6-oxo-4-pyrimidinecarboxamide;
N-[(4-fluoro-3-methylphenyl)methyl]-2-(8-azaspiro[4.5]dec-8-yl)-1,6-dihydro-5-hydroxy-1-methyl-6-oxo-4-pyrimidinecarboxamide;
N-[(4-fluoro-3-methylphenyl)methyl]-2-[3-[[(4-fluoro-3-methylphenyl)methyl]amino]spiro[1H-indene-1,4'-piperidin]-1'-yl]-1,6-dihydro-5-hydroxy-1-methyl-6-oxo-4-pyrimidinecarboxamide;
N-[(4-fluoro-3-methylphenyl)methyl]-2-(8-azaspiro[4.5]dec-8-yl)-1,6-dihydro-5-hydroxy-1-methyl-6-oxo-4-pyrimidinecarboxamide;
N-(4-fluoro-3-methylbenzyl)-5-hydroxy-1-methyl-6-oxo-2-(1-ethanone)-2,8-diazaspiro[4.5]dec-8-yl)-1,6-dihydropyrimidine-4-carboxamide;
N-(4-fluoro-3-methylbenzyl)-5-hydroxy 1-methyl-6-oxo-2-(1-trimethylsilane-6-azaspiro[4.3]oct-6-yl)-1,6-dihydropyrimidine-4-carboxamide;
N-(4-fluoro-3-methylbenzyl)-5-hydroxy-1-methyl-6-oxo-2-(6-azaspiro[4.3]oct-6-yl)-1,6-dihydropyrimidine-4-carboxamide; and
N-[(4-fluoro-3-methylphenyl)methyl]-1,6-dihydro-5-hydroxy-1-methyl-2-(1-oxa-8-azaspiro[4.5]dec-8-yl)-6-oxo-4-pyrimidinecarboxamide.

9. A compound selected from
N-[(4-fluorophenyl)methyl]-1,6-dihydro-5-hydroxy-1-methyl-6-oxo-2-(7-azaspiro[4.5]dec-7-yl)-4-pyrimidinecarboxamide;
N-[(4-fluorophenyl)methyl]-1,6-dihydro-5-hydroxy-1-methyl-6-oxo-2-(6-oxa-9-azaspiro[4.5]dec-9-yl)-4-pyrimidinecarboxamide;
N-[(4-fluorophenyl)methyl]-1,6-dihydro-5-hydroxy-1-methyl-6-oxo-2-(2-oxa-7-azaspiro[4.5]dec-7-yl)-4-pyrimidinecarboxamide;
N-[(4-fluorophenyl)methyl]-1,6-dihydro-5-hydroxy-1-methyl-6-oxo-2-(1,3-dioxo-2,7-diazaspiro[4.5]dec-7-yl)-4-pyrimidinecarboxamide;

N-[(4-fluorophenyl)methyl]-1,6-dihydro-5-hydroxy-1-methyl-6-oxo-2-(2-oxo-1,7-diazaspiro[4.5]dec-7-yl)-4-pyrimidinecarboxamide;

N-[(4-fluorophenyl)methyl]-1,6-dihydro-5-hydroxy-1-methyl-6-oxo-2-(2,4-dioxo-1,3,8-triazaspiro[4.5]dec-8-yl)-4-pyrimidinecarboxamide;

N-[(4-fluorophenyl)methyl]-1,6-dihydro-5-hydroxy-1-methyl-6-oxo-2-(8-azaspiro[4.5]dec-8-yl)-4-pyrimidinecarboxamide;

N-[(4-fluorophenyl)methyl]-1,6-dihydro-5-hydroxy-1-methyl-6-oxo-2-(1-oxa-8-azaspiro[4.5]dec-8-yl)-4-pyrimidinecarboxamide;

N-[(4-fluorophenyl)methyl]-1,6-dihydro-5-hydroxy-1-methyl-6-oxo-2-(1-oxo-2,8-diazaspiro[4.5]dec-8-yl)-4-pyrimidinecarboxamide;

N-[(4-fluorophenyl)methyl]-1,6-dihydro-5-hydroxy-1-methyl-6-oxo-2-(2-oxo-1,3,8-triazaspiro[4.5]dec-8-yl)-4-pyrimidinecarboxamide;

N-[(4-fluorophenyl)methyl]-1,6-dihydro-5-hydroxy-1-methyl-6-oxo-2-(1,3,8-triazaspiro[4.5]deca-1,3-dien-8-yl)-4-pyrimidinecarboxamide;

N-[(4-fluorophenyl)methyl]-1,6-dihydro-5-hydroxy-1-methyl-6-oxo-2-(3-oxa-9-azaspiro[5.5]undec-9-yl)-4-pyrimidinecarboxamide;

N-[(4-fluorophenyl)methyl]-1,6-dihydro-5-hydroxy-1-methyl-6-oxo-2-(1-oxa-9-azaspiro[5.5]undec-9-yl)-4-pyrimidinecarboxamide;

N-[(4-fluorophenyl)methyl]-1,6-dihydro-5-hydroxy-1-methyl-6-oxo-2-(1-oxa-3,8-diazaspiro[4.5]dec-2-en-8-yl)-4-pyrimidinecarboxamide;

N-[(4-fluorophenyl)methyl]-1,6-dihydro-5-hydroxy-1-methyl-6-oxo-2-(1-oxa-4,9-diazaspiro[5.5]undec-9-yl)-4-pyrimidinecarboxamide;

N-[(4-fluorophenyl)methyl]-1,6-dihydro-5-hydroxy-1-methyl-6-oxo-2-(5-oxo-1-oxa-4,9-diazaspiro[5.5]undec-9-yl)-4-pyrimidinecarboxamide;

N-[(4-fluorophenyl)methyl]-1,6-dihydro-5-hydroxy-1-methyl-6-oxo-2-(1,4,9-triazaspiro[5.5]undec-9-yl)-4-pyrimidinecarboxamide; and N-[(4-fluorophenyl)methyl]-1,6-dihydro-5-hydroxy-1-methyl-6-oxo-2-(5-oxo-1,4,9-triazaspiro[5.5]undec-9-yl)-4-pyrimidinecarboxamide.

10. A composition comprising a pharmaceutically acceptable amount of a compound of claim 1 and a pharmaceutically acceptable carrier.

11. A method of treating HIV-1 infection in a patient comprising administering a therapeutically effective amount of a compound of claim 1.

* * * * *